US008565886B2

(12) United States Patent
Nelson et al.

(10) Patent No.: US 8,565,886 B2
(45) Date of Patent: Oct. 22, 2013

(54) AROUSAL STATE MODULATION WITH ELECTRICAL STIMULATION

(75) Inventors: Dwight E. Nelson, Shoreview, MN (US); Jianping Wu, Shoreview, MN (US); Jonathon E. Giftakis, Maple Grove, MN (US); Mark T. Rise, Monticello, MN (US)

(73) Assignee: Medtronic, Inc., Minneapolis, MN (US)

( * ) Notice: Subject to any disclaimer, the term of this patent is extended or adjusted under 35 U.S.C. 154(b) by 4 days.

(21) Appl. No.: 13/288,797

(22) Filed: Nov. 3, 2011

(65) Prior Publication Data
US 2012/0116475 A1 May 10, 2012

Related U.S. Application Data

(60) Provisional application No. 61/412,052, filed on Nov. 10, 2010.

(51) Int. Cl.
*A61N 1/18* (2006.01)
(52) U.S. Cl.
USPC .......................................................... 607/45
(58) Field of Classification Search
USPC .......................................................... 607/45
See application file for complete search history.

(56) References Cited

U.S. PATENT DOCUMENTS

| 5,938,688 A | 8/1999 | Schiff |
| 6,066,163 A | 5/2000 | John |
| 6,263,237 B1 | 7/2001 | Rise |
| 6,463,328 B1 | 10/2002 | John |
| 6,539,263 B1 * | 3/2003 | Schiff et al. ..................... 607/45 |
| 6,622,036 B1 | 9/2003 | Suffin |
| 6,671,555 B2 | 12/2003 | Gielen et al. |
| 6,708,064 B2 | 3/2004 | Rezai |
| 7,006,872 B2 | 2/2006 | Gielen et al. |
| 7,024,247 B2 | 4/2006 | Gliner et al. |
| 7,231,245 B2 | 6/2007 | Greenwald et al. |

(Continued)

FOREIGN PATENT DOCUMENTS

| EP | 1559369 A1 | 8/2005 |
| WO | 0176469 A2 | 10/2001 |

(Continued)

OTHER PUBLICATIONS

Babiloni et al., "Ibuprofen treatment modifies cortical sources of EEG rhythms in mild Alzheimer's disease," Clinical Neurophysiology 120, pp. 709-718, Feb. 2009.

(Continued)

*Primary Examiner* — Carl H Layno
*Assistant Examiner* — Paula J Stice
(74) *Attorney, Agent, or Firm* — Shumaker & Sieffert, P.A.

(57) ABSTRACT

In some examples, an arousal network of a brain of a patient can be activated to modify the arousal state of the patient, which may be useful in treating a cognitive disorder of the patient. In some examples, a bioelectrical brain signal indicative of electrical activity in a first portion of the brain is monitored to determine whether the patient is in a first arousal state, and, in response to determining the patient is in the first arousal state, electrical stimulation is delivered to a second portion of the brain to activate an arousal neural network in the first portion of the brain to induce a second arousal state to treat the cognitive disorder, where the second arousal state is different than the first arousal state.

34 Claims, 5 Drawing Sheets

(56) References Cited

U.S. PATENT DOCUMENTS

| | | |
|---|---|---|
| 7,277,758 B2 | 10/2007 | DiLorenzo |
| 7,353,064 B2 | 4/2008 | Gliner et al. |
| 7,353,065 B2 | 4/2008 | Morrell |
| 7,418,290 B2 | 8/2008 | Devlin et al. |
| 7,519,431 B2 | 4/2009 | Goetz et al. |
| 2001/0031993 A1 | 10/2001 | Salo et al. |
| 2002/0013612 A1 | 1/2002 | Whitehurst |
| 2004/0093983 A1 | 5/2004 | Mishima et al. |
| 2004/0111127 A1 | 6/2004 | Gliner |
| 2005/0043774 A1 | 2/2005 | Devlin et al. |
| 2005/0081847 A1 | 4/2005 | Lee et al. |
| 2005/0197590 A1* | 9/2005 | Osorio et al. .......... 600/544 |
| 2005/0216064 A1 | 9/2005 | Heruth et al. |
| 2005/0216071 A1 | 9/2005 | Devlin et al. |
| 2006/0004422 A1 | 1/2006 | De Ridder |
| 2006/0058627 A1 | 3/2006 | Flaherty et al. |
| 2006/0212090 A1 | 9/2006 | Lozano et al. |
| 2006/0259099 A1 | 11/2006 | Goetz et al. |
| 2006/0264957 A1 | 11/2006 | Cragg et al. |
| 2007/0027500 A1 | 2/2007 | Maschino et al. |
| 2007/0028212 A1 | 2/2007 | Meijer et al. |
| 2007/0123758 A1 | 5/2007 | Miesel et al. |
| 2007/0129769 A1 | 6/2007 | Bourget et al. |
| 2007/0142874 A1 | 6/2007 | John |
| 2007/0150024 A1 | 6/2007 | Leyde et al. |
| 2007/0161919 A1 | 7/2007 | DiLorenzo |
| 2007/0167991 A1 | 7/2007 | DiLorenzo |
| 2007/0173901 A1 | 7/2007 | Reeve |
| 2007/0208212 A1 | 9/2007 | DiLorenzo |
| 2007/0265536 A1 | 11/2007 | Giftakis et al. |
| 2007/0293901 A1 | 12/2007 | Rousso et al. |
| 2008/0033502 A1 | 2/2008 | Harris et al. |
| 2008/0249431 A1 | 10/2008 | Bier et al. |
| 2008/0269631 A1 | 10/2008 | Denison et al. |
| 2009/0082641 A1 | 3/2009 | Giftakis et al. |
| 2009/0082691 A1 | 3/2009 | Denison et al. |
| 2009/0264957 A1 | 10/2009 | Giftakis et al. |
| 2009/0264967 A1 | 10/2009 | Giftakis et al. |
| 2010/0121214 A1 | 5/2010 | Giftakis et al. |
| 2011/0029038 A1* | 2/2011 | Hyde et al. .......... 607/45 |

FOREIGN PATENT DOCUMENTS

| | | |
|---|---|---|
| WO | 2004034882 A2 | 4/2004 |
| WO | 2006092061 A1 | 9/2006 |
| WO | 2008013722 A1 | 1/2008 |
| WO | 2009129486 A2 | 10/2009 |

OTHER PUBLICATIONS

Stefani et al., "Non-motor functions in parkinsonian patients implanted in the pedunculopontine nucleus: Focus on sleep and cognitive domains," Journal of the Neurological Sciences, doi: 10.1016/j.jns.2009.08.017, 5 pgs., 2009.

Kempf et al., "Gamma activity and reactivity in human thalamic local field potentials," European Journal of Neuroscience, vol. 29, pp. 943-953, Jan. 2009.

Cantero et al., "Increased synchronization and decreased neural complexity underlie thalamocortical oscillatory dynamics in mild cognitive impairment," NeuroImage 46, pp. 938-948, Mar. 2009.

Freund et al., "Cognitive Functions in a Patient With Parkinson-Dementia Syndrome Undergoing Deep Brain Stimulation," Arch Neurol, vol. 66, No. 6, 5 pgs., Jun. 2009.

Jutras et al., "Gamma-Band Synchronization in the Macaque Hippocampus and Memory Formation," The Journal of Neuroscience, 29(40), pp. 12521-12531, Oct. 2009.

Erwin B. Montgomery, Jr., M.D, "Deep Brain Stimulation Programming," Feb. 20, 2006, 37 pages.

Wright et al., "Cortical excitability predicts seizures in acutely drug-reduced temporal lobe epilepsy patients," Neurology, 2006;67:1646-1651.

U.S. Appl. No. 61/266,424, filed Dec. 3, 2009 entitled "Selecting Therapy Cycle Parameters Based on Monitored Brain Signal,".

U.S. Appl. No. 12/843,665, filed Jul. 26, 2010 entitled "Selecting Therapy Cycle Parameters Based on Monitored Brain Signal,".

International Search Report and Written Opinion dated Jan. 5, 2012 for corresponding PCT Application No. PCT/US2011/059748, (13 pgs.).

* cited by examiner

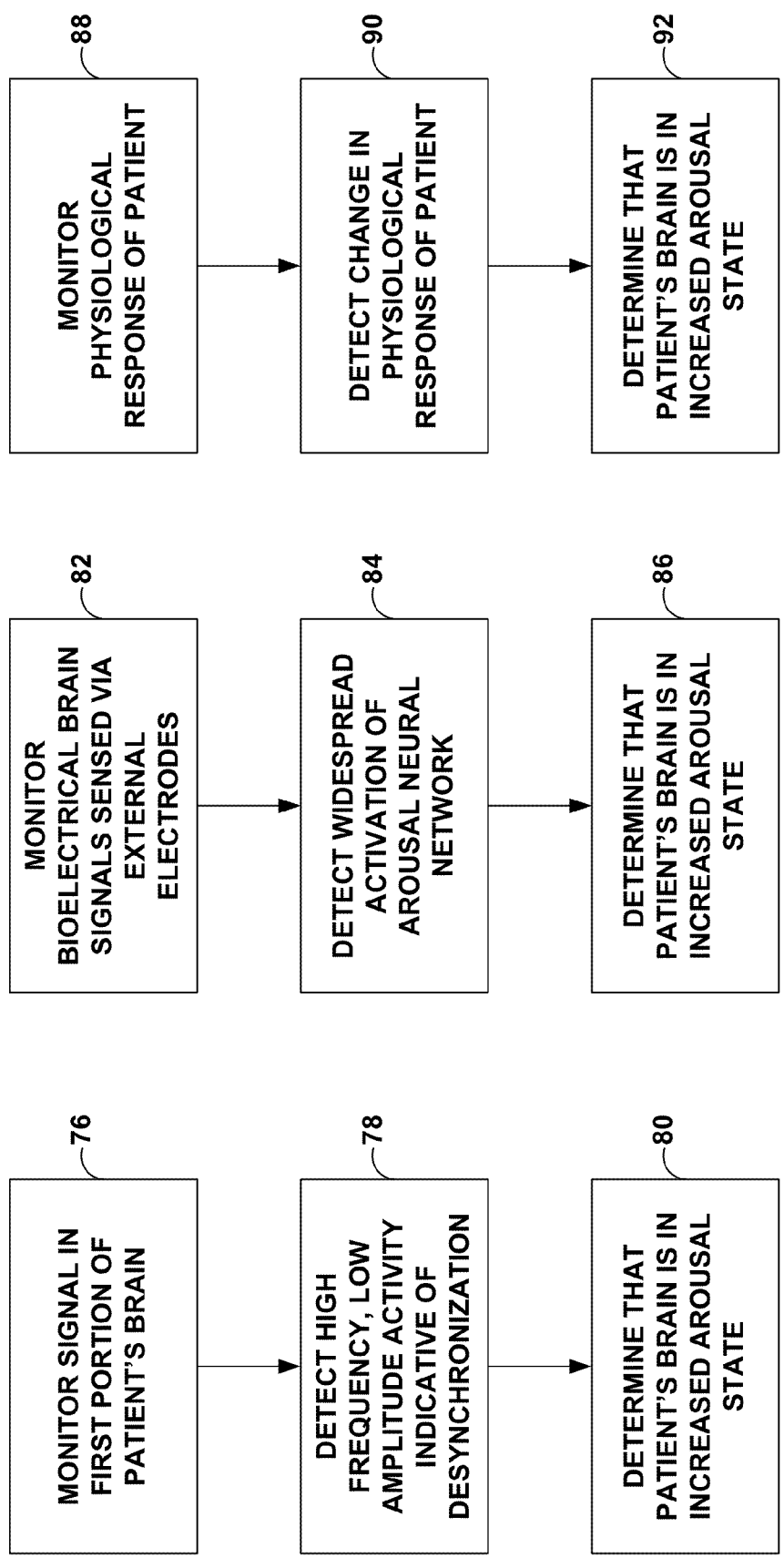

AROUSAL STATE MODULATION WITH ELECTRICAL STIMULATION

This application claims the benefit of U.S. Provisional Application No. 61/412,052, entitled, "AROUSAL STATE MODULATION WITH ELECTRICAL STIMULATION," and filed on Nov. 10, 2010, the entire content of which is incorporated herein by reference.

TECHNICAL FIELD

The disclosure relates to medical systems, and, more particularly, medical systems that deliver electrical stimulation to a brain of a patient.

BACKGROUND

Implantable medical devices, such as electrical stimulation devices, have been proposed for use in different therapeutic applications, such as for deep brain stimulation (DBS), spinal cord stimulation (SCS), pelvic stimulation, gastric stimulation, peripheral nerve stimulation, or functional electrical stimulation of a target tissue site within a patient. An electrical stimulation device may be used to treat a variety of symptoms or conditions of a patient, such as chronic pain, tremor, Alzheimer's disease, Parkinson's disease, other types of movement disorders, seizure disorders (e.g., epilepsy), urinary or fecal incontinence, sexual dysfunction, obesity, mood disorders, gastroparesis, or diabetes. In some therapy systems, an implantable electrical stimulator delivers electrical therapy to a target tissue site within a patient with the aid of one or more electrodes, which may be deployed by medical leads.

SUMMARY

In general, the disclosure relates to modulating an arousal state in a brain of a patient and methods, systems, and devices for modeling the arousal state in the brain. An arousal neural network in the brain of a patient can be activated in order to modulate the arousal state. In some examples, activating an arousal neural network in the patient's brain can induce arousal in the patient's brain, which can be useful for treating (e.g., mitigating one or more symptoms or otherwise improving the patient condition) a neurological disorder of the patient, such as Alzheimer's disease.

In some examples described herein, a bioelectrical brain signal indicative of electrical activity in a first portion of the brain of the patient is monitored to determine whether the brain of the patient is in a first arousal state, e.g., a reduced arousal state. Based on a determination that the brain of the patient is in the first arousal state, e.g., in response to the determination, electrical stimulation can be delivered to a second portion of the brain of the patient. The electrical stimulation is configured to activate an arousal neural network in the first portion of the brain of the patient to induce a second arousal state, e.g., an increased arousal state, in the brain of the patient. The second portion of the brain of the patient is different than the first portion.

In one example, the disclosure is directed to a method that includes receiving, from a sensing module, a bioelectrical brain signal indicative of electrical activity in a first portion of a brain of a patient, determining, with a processor, that the brain of the patient is in a first arousal state based on at least one characteristic of the bioelectrical brain signal, and controlling, with the processor, a stimulation module to deliver electrical stimulation to a second portion of the brain of the patient that is different than the first portion in response to determining that the first portion of the brain of the patient is in the first arousal state. The electrical stimulation may be configured to activate an arousal neural network in the first portion of the brain of the patient to induce a second arousal state in the brain of the patient. The electrical stimulation may be configured to treat a cognitive disorder of the patient In another example, the disclosure is directed to a system that includes a sensing module configured to sense a bioelectrical brain signal indicative of electrical activity in a first portion of a brain of a patient, a processor configured to determine that the brain of the patient is in a first arousal state based on at least one characteristic of the bioelectrical brain signal, and a stimulation generator configured to generate and deliver electrical stimulation to a second portion of the brain of the patient that is different than the first portion. The processor is configured to control the stimulation generator to deliver electrical stimulation to the second portion of the brain of the patient in response to determining that the first portion of the brain of the patient is in the first arousal state. The electrical stimulation is configured to activate an arousal neural network in the first portion of the brain of the patient to induce a second arousal state in the brain of the patient, and the electrical stimulation is configured to treat a cognitive disorder of the patient.

In another example, the disclosure is directed to a computer-readable medium that includes instructions that cause a programmable processor to receive, from a sensing module, a bioelectrical brain signal indicative of electrical activity in a first portion of a brain of a patient, determine that the brain of the patient is in a first arousal state based on at least one characteristic of the bioelectrical brain signal, and control a stimulation generator to deliver electrical stimulation to a second portion of the brain of the patient in response to determining that the first portion of the brain of the patient is in the first arousal state. The electrical stimulation is configured to activate an arousal neural network in the first portion of the brain of the patient to induce a second arousal state in the brain of the patient, and the electrical stimulation is configured to treat a cognitive disorder of the patient. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

In another example, the disclosure is directed to a system that includes means for receiving a bioelectrical brain signal indicative of electrical activity in a first portion of a brain of a patient, means for determining that the brain of the patient is in a first arousal state based on at least one characteristic of the bioelectrical brain signal, and means for delivering electrical stimulation to a second portion of the brain of the patient that is different than the first portion in response to determining that the first portion of the brain of the patient is in the first arousal state. The electrical stimulation is configured to activate an arousal neural network in the first portion of the brain of the patient to induce a second arousal state in the brain of the patient, and the electrical stimulation is configured to treat a cognitive disorder of the patient.

In another aspect, the disclosure is directed to an article of manufacture comprising a computer-readable storage medium. The computer-readable storage medium comprises computer-readable instructions for execution by a processor.

The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more examples are set forth in the accompanying drawings and the description below. Other features, objects, and advantages will be apparent from the description and drawings, and from the claims.

BRIEF DESCRIPTION OF DRAWINGS

FIGS. 6A, 6B, and 6C are flow diagrams illustrating example techniques for determining whether a brain of a patient is in an increased arousal state.

DETAILED DESCRIPTION

Figure 1:
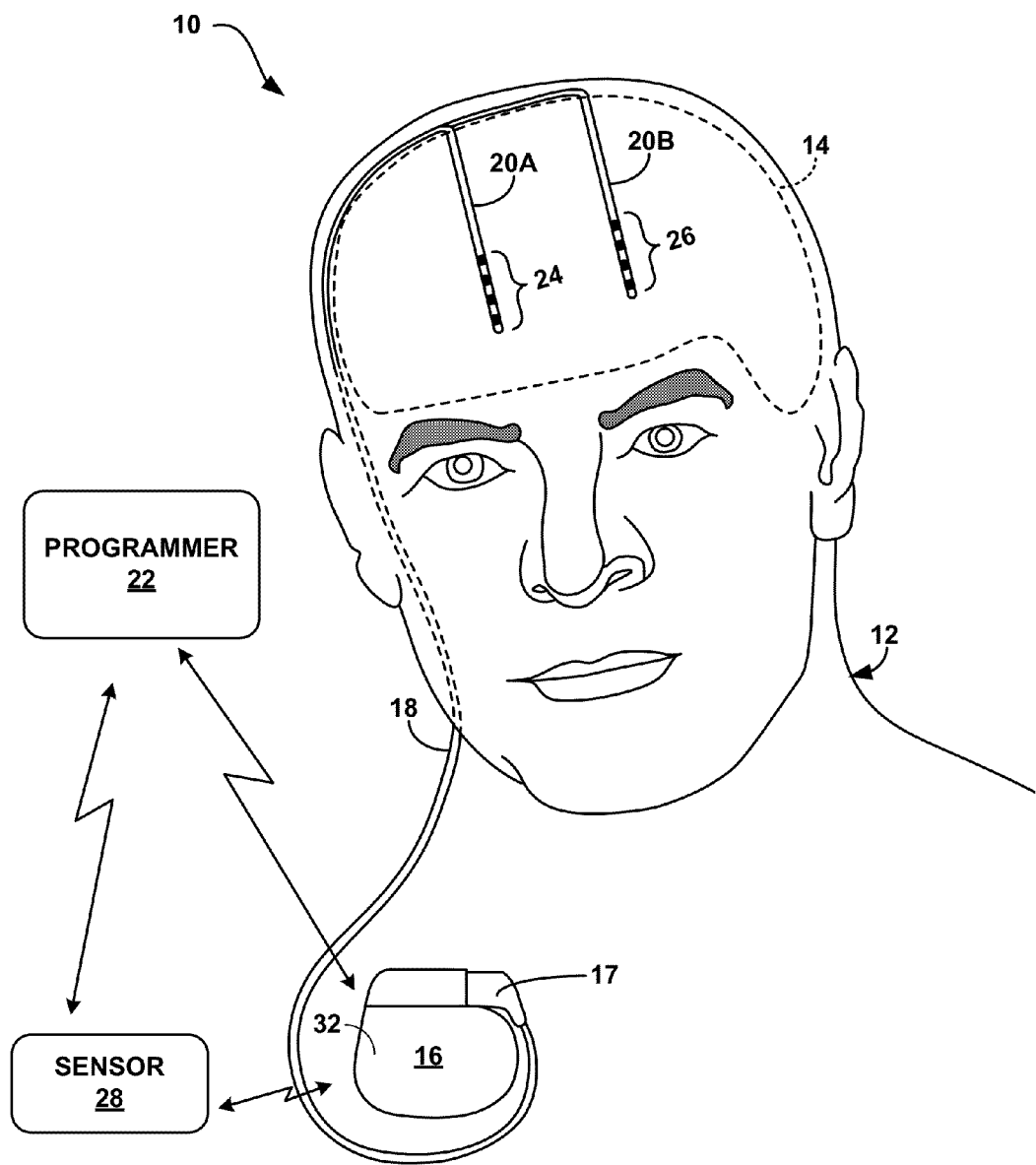
FIG. 1 is a conceptual diagram illustrating an example therapy system that delivers therapy to a patient to manage a disorder of the patient.

The methods, systems, and devices described provide therapy to a patient by delivering electrical stimulation to activate an arousal neural network in a patient's brain. An arousal neural network may be a network of nerves that are interconnected, such that information is transmitted through the network of nerves, where activation of the arousal neural network may induce arousal in the patient's brain. Generally, arousal is referred to herein as a state of the patient's brain that causes the patient to be reactive to stimuli, which may help the patient capture information better than when the brain of the patient is in a less aroused state. An increased arousal state can be characterized by an improvement in the patient's cognitive function. Improvement in the patient's cognitive function can be indicated by, for example, an improved ability of the patient to acquire new memories or in improvement in reaction time to stimuli in the patient's environment. Additionally or alternatively, the increased arousal state can be characterized by an improvement in communication between one or more structures of the brain at one or more frequency bands of a bioelectrical signal.

In examples in which a patient suffers from a neurological disorder such as Alzheimer's disease, the patient may have reduced ability to enter an arousal state and, consequently, may have reduced ability to react to stimuli, which can result in a decline in cognitive function of the patient. For example, in some examples, the patient's neurological disorder may be characterized by an inability to acquire new memories, which may result from the patient's reduced ability to react to stimuli in the patient's environment.

The electrical stimulation described herein may activate an arousal neural network in the patient's brain to induce arousal (e.g., increase the level of arousal) in the patient's brain, which can cause the patient to be more vigilant and/or attentive to stimuli, e.g., characteristics of the surrounding environment or ongoing events. Increased arousal of the patient's brain may result in improved cognitive function, such as by activating the memory system of the brain. For example, in examples in which the patient's neurological disorder is characterized by an inability to acquire new memories, increased arousal of the patient's brain may improve the patient's ability to acquire new memories and improve the patient's ability to capture information. In some cases, the inability to acquire new memories may be a condition associated with Alzheimer's disease. The electrical stimulation therapy described herein may be an approach to treating Alzheimer's disease, as well as other neurological disorders, that addresses the cognitive state of the patient. This may differ in some cases from existing Alzheimer's disease treatments that specifically target improving only the memory of the patient.

Alzheimer's disease may physiologically be characterized by deposits, e.g., plaques and tangles, which form within the neural networks of the brain of the patient. Accumulation of these deposits may interfere with learning and cognition of the patient, e.g., due to the loss of synapses and cell death. For example, accumulation of these deposits in the brain of the patient may interfere with cortical activity, e.g., as compared to those patients without Alzheimer's disease or similar deposits. In some examples, the effects of these deposits within the brain can be observed based on a bioelectrical brain signal, e.g., an electroencephalogram (EEG) signal or an electrocorticogram (ECoG), indicative of activity within particular structures, e.g., the cortex and thalamus structures, of the brain. The slowing of the bioelectrical brain signal may, in some examples, be identified by at least one of lack of normal, high frequency oscillations in the bioelectrical brain signal, disrupted frequency matching of oscillations between various regions of the brain, reduced phase locking of oscillations, or pathological synchronization across regions of the brain.

The electrical stimulation described herein may at least partially act to counter the effects of the deposits that may be present within the brain of a patient with Alzheimer's disease by re-establishing more normal, high frequency oscillations in affected areas of the brain, which may lead to reduction or alleviation of symptoms of patient. For example, by delivering electrical stimulation to the brain of the patient using techniques described herein to increase an arousal state of a brain of a patient, the reduction in cortical activity attributable to the deposits in the brain may be at least partially overcome. Thus, in some patients with Alzheimer's disease, the electrical stimulation described herein is delivered to the brain of the patient to increase the arousal state of the brain to an arousal state above a baseline arousal state of the brain (e.g., in the absence of any electrical stimulation or relative to a patient without Alzheimer's disease).

Examples described herein include sensing bioelectrical brain activity within a first portion of the brain of a patient, and, upon determining the first portion of the brain is in a relatively low arousal state, delivering stimulation to a second portion of the brain, which is different than the first portion and does not overlap or only partially overlaps with the first portion. In some examples, the first and second portions of the brain are in different anatomical structures of the brain. The second portion of the brain is within a common arousal neural network as the first portion, such that stimulation delivered to the second portion traverses through the neural network of the brain to the first portion. By delivering stimulation to the second portion of the brain rather than directly to the first portion, the first portion of the brain may be aroused to a physiologically significant level. The physiologically significant level may be a level at which the cognitive function of the patient is improved, as indicated by established cognitive tests or observed by a patient caretaker or clinician.

While delivering stimulation directly to the first portion of the brain may be useful, it is believed that, in some cases, activating the arousal network of which the first portion of the brain is part by stimulating the second portion of the brain may be more effective in managing some neurological disorders, such as Alzheimer's disease. Stimulation delivered to the second portion of the brain, rather than directly to the first portion, may have broader outputs to larger areas of the brain outside and including the second portion of the brain. In some examples, the second portion of the brain may be a more posterior region than the first portion of the brain, such that electrical stimulation of the second portion activates a relatively larger area within the brain of the patient than electrical stimulation of the first portion directly. In some examples, the posterior region may be sublimbic to the first portion of the brain, and the stimulation of the sublimbic region of the brain may activate limbic structures, which may include the first portion of the brain.

Regions of the brain that are more posterior than frontal may be responsible for activation of larger portions of brain (e.g., larger neural networks), e.g., due to the arrangement of neurons within the brain, and, consequently, stimulation of more posterior portions may cause activation of a larger portion of the brain than stimulation of more frontal portions. This can be referred to as "global activation" of the brain. Thus, in some examples, delivering stimulation to the second portion of the brain to increase an arousal state of a first portion may be more efficacious for a particular patient condition (e.g., Alzheimer's disease) for a particular patient than delivering stimulation directly to the first portion. For example, delivering stimulation to the second portion of the brain may better activate an arousal network of the brain, where the arousal network includes the first portion of the brain. The better activation of the arousal network can be characterized by, for example, desynchronization of the bioelectrical brain signal sensed in the first portion of the brain. In contrast, delivering stimulation directly to the first portion may not induce as high of an arousal state, where the level of the arousal state may be characterized by less desynchronization of the bioelectrical brain signal sensed in the first portion and/or by an improvement in the patient's cognitive function.

In addition, delivering stimulation to the second portion of the brain, which may activate a larger portion of the brain than delivering stimulation to the first portion, may be a more efficient use of stimulation energy. It may be desirable to deliver a lower intensity stimulation (e.g., which can be a function of one or more stimulation parameter values, such as amplitude and frequency) in order to increase the efficiency of stimulation (e.g., the energy usage by the IMD to generate the stimulation) in order to conserve the power source of the IMD, as well as to minimize the patient's adaptation to the stimulation.

FIG. 1 is a conceptual diagram illustrating an example therapy system 10 that delivers therapy to patient 12 to manage a disorder of patient 12. In some examples, therapy system 10 may deliver therapy to patient 12 to manage a neurological disorder of patient 12. For example, therapy system 10 may provide therapy to manage symptoms of a psychological disorder, a mood disorder, a movement disorder, a cognitive disorder, a sleep disorder, a seizure disorder, or a neurodegenerative impairment. In some examples, therapy system 10 may provide therapy to patient 12 to manage Alzheimer's disease. Patient 12 ordinarily will be a human patient. In some cases, however, therapy system 10 may be applied to other mammalian or non-mammalian non-human patients. While examples of the disclosure are described with regard to treatment of a cognitive disorder such as Alzheimer's disease, in other examples, therapy system 10 may provide therapy to manage symptoms of other patient conditions.

Therapy system 10 includes implantable medical device (IMD) 16, lead extension 18, one or more leads 20A and 20B (collectively "leads 20") with respective sets of electrodes 24, 26, medical device programmer 22, and sensor 28, which may be external to patient 12 or implanted within patient 12. IMD 16 includes a therapy module that includes a stimulation generator that generates and delivers electrical stimulation therapy to one or more regions of brain 14 of patient 12 via the electrodes 24, 26 of leads 20A and 20B, respectively. In the example shown in FIG. 1, therapy system 10 may be referred to as deep brain stimulation (DBS) system because IMD 16 provides electrical stimulation therapy directly to tissue within brain 14, e.g., a tissue site under the dura mater of brain 14. In other examples, leads 20 may be positioned to deliver therapy to a surface of brain 14, e.g., the cortical surface of brain 14.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via a connector block (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 14. IMD 16 is constructed of a biocompatible material that resists corrosion and degradation from bodily fluids. IMD 16 may comprise a hermetic housing 32 to substantially enclose components, such as a processor, therapy module, and memory.

Electrical stimulation may be delivered to one or more regions of brain 14, which may be selected based on many factors, such as the type of patient condition for which therapy system 10 is implemented to manage. In some examples, leads 20 may be implanted within the right and left hemispheres of brain 14 (e.g., as illustrated in FIG. 1) while, in other examples, both of leads 20 may be implanted within one of the right or left hemispheres. Other implant sites for leads 20 and IMD 16 are contemplated. For example, in some examples, IMD 16 may be implanted on or within cranium 32. In addition, in some examples, leads 20 may be coupled to a single lead that is implanted within one hemisphere of brain 14 or implanted through both right and left hemispheres of brain 14.

Leads 20 may be positioned to deliver electrical stimulation to one or more target tissue sites within brain 14 to manage patient symptoms associated with a disorder of patient 12. Leads 20 may be implanted to position electrodes 24, 26 at desired locations of brain 14 through respective holes in cranium 32. Leads 20 may be placed at any location within brain 14 such that electrodes 24, 26 are capable of providing electrical stimulation to target tissue sites within brain 14 during treatment. Different neurological or psychiatric disorders may be associated with activity in one or more regions of brain 14, which may differ between patients. As described in further detail below, in some examples, activity in the cortex and thalamus may be indicative of an Alzheimer's state (e.g., a state in which one or more symptoms of Alzheimer's disease are observed by patient 12, a patient caretaker or a clinician, or a state in which synchronization of a bioelectrical brain signal sensed in the cortex or thalamus is observed).

In the example shown in FIG. 1, electrodes 24, 26 of leads 20 are shown as ring electrodes. Ring electrodes may be relatively easy to program and are typically capable of delivering an electrical field to any tissue adjacent to leads 20 (e.g., in all directions away from an outer perimeter of leads 20). In other examples, electrodes 24, 26 of leads 20 may have different configurations. For example, electrodes 24, 26 of leads 20 may have a complex electrode array geometry that is capable of producing shaped electrical fields. The complex electrode array geometry may include multiple electrodes (e.g., partial ring or segmented electrodes) around the perimeter of each lead 20, rather than a ring electrode. In this manner, electrical stimulation may be directed to a specific direction from leads 20 (e.g., in a direction less than around the entire outer perimeter of leads 20) to enhance therapy efficacy and reduce possible adverse side effects from stimulating a large volume of tissue. In some examples, outer housing 32 of IMD 16 may include one or more stimulation and/or sensing electrodes. For example, housing 32 can comprise an electrically conductive material that is exposed to tissue of patient 12 when IMD 16 is implanted in patient 12, or an electrode can be attached to housing 32. In alternative examples, leads 20 may have shapes other than elongated cylinders as shown in FIG. 1. For example, leads 20 may be paddle leads, spherical leads, bendable leads, or any other type of shape effective in treating patient 12.

In some examples, the location of the electrodes 24, 26 within brain 14 can be determined based on analysis of a bioelectrical brain signal of the patient sensed via one or more of the electrodes 24, 26. For example, a particular physiological structure (e.g., the amygdala) may exhibit a unique electrical signal and, thus, facilitate positioning of the electrodes of the lead at the desired implant location (e.g., near the target tissue) through monitoring of the bioelectrical brain signal.

In the examples described herein, for treatment of a cognitive disorder (e.g., Alzheimer's disease), leads 20 may be implanted to deliver electrical stimulation to various portions of brain 14 of patient 12, such as the anterior thalamic nucleus, the internal capsule, the cingulate cortex (including the anterior cingulate gyms), the formix, the mammillary bodies, the mammillothalamic tract (mammillothalamic fasciculus), the hippocampus, the Basal Nucleus of Meynert (NBM), the medial septal nucleus, the thalamic reticular nucleus the orbitofrontal cortex, the locus coeruleus, the raphe nucleus, the substantia nigra, the amygdala, the interior thalamus, the hypothalamus, and other portions of the thalamus and the limbic system. These portions of brain 14 may be referred to as the "second portion" in some examples described herein. In some examples, leads 20 may be implanted to deliver electrical stimulation to portions of brain 14 that are more posterior than frontal such that electrical stimulation activates a relatively large portion of brain 14. That is, portions of brain 14 that are more posterior than frontal may be responsible for activation of larger portions of brain 14 (e.g., larger neural networks) and, consequently, stimulation of posterior portions may cause activation of a larger portion of brain 14 than stimulation of more frontal portions.

As described above, delivery of stimulation to a more posterior portion of brain 14 (e.g., the second portion of brain 14) may activate an arousal neural network in a first portion of brain 14, which is more frontal than the posterior portion, because the posterior portion may have broader outputs to larger areas of brain 14. This may be attributable at least in part to the arrangement of neurons within brain 14, which may result in stimulation of more posterior portions activating of a larger portion of the brain than stimulation of more frontal portions.

As described in further detail below, in the examples described herein, IMD 16 delivers therapy to any suitable portion of brain 14 that may play a role in affecting an arousal state in brain 14 (e.g., as indicated by electrical signals sensed in brain 14) by activating an arousal neural network in brain 14 to treat a cognitive disorder of patient 12. For example, IMD 16 may deliver therapy to a second portion of brain 14 via a selected subset of electrodes 24, 26 to increase activity of an arousal neural network in a first portion of brain 14.

Figure 5:
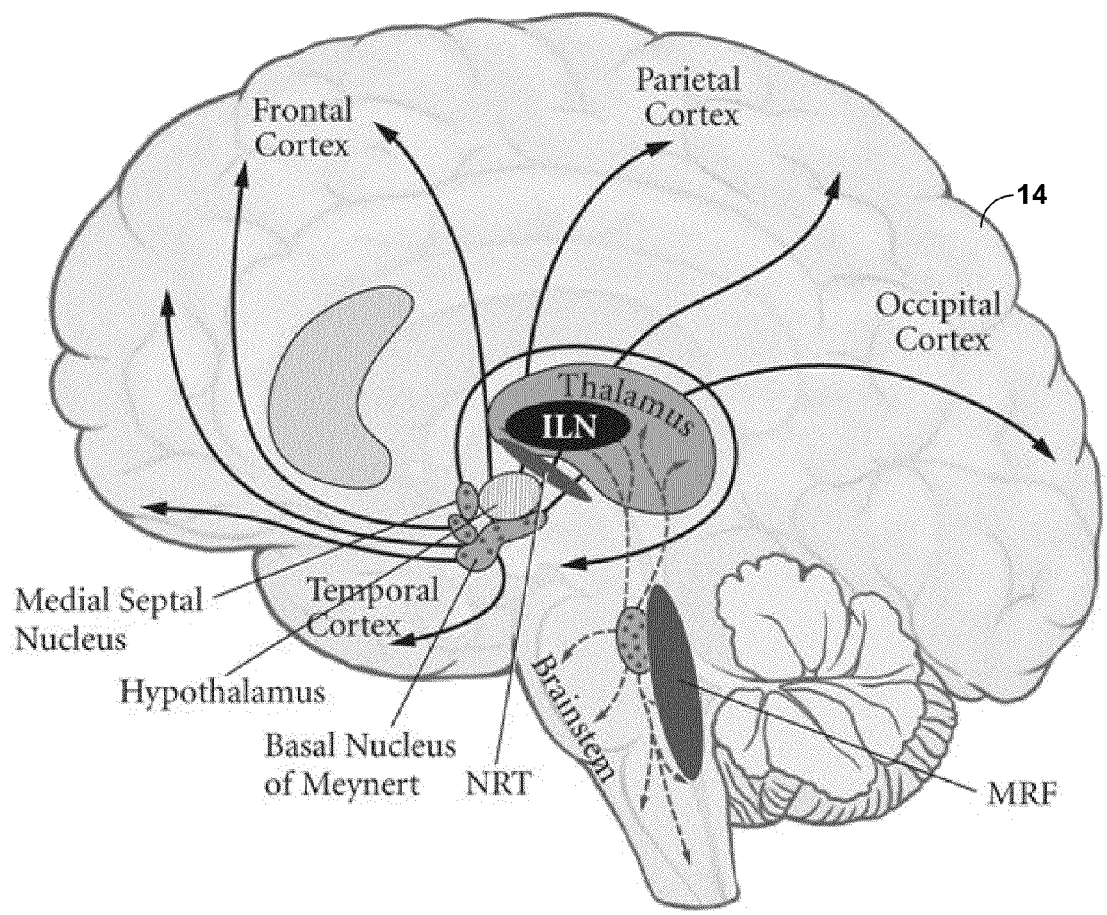
FIG. 5 is a conceptual diagram illustrating several neural connections that may play a role in inducing arousal in a brain of a patient.

The electrical stimulation delivered to the portions of brain 14 described above may, in some examples, activate one or more arousal neural networks within brain 14 in order to modulate the arousal state of brain 14. For example, in some examples, the electrical stimulation may activate the arousal network in a cortex or thalamus of brain 14. One arousal network can include, for example, a medullary reticular formation (MRF) and the thalamus (as shown in FIG. 5). The thalamus may be, for example, the first portion of brain 14 and the MRF may be the second portion of brain 14 to which therapy is delivered in order to activate the thalamus and increase the arousal state of the thalamus. Another arousal network may include the Basal Nucleus of Meynert and cortex (as shown in FIG. 5, the Basal Nucleus of Meynert outputs to the cortex). Another arousal network may include the hypothalamus and the cortex. In these examples, the cortex may be the first portion of brain 14 and the Basal Nucleus of Meynert and/or hypothalamus may be the second portion of brain 14 to which therapy is delivered in order to increase the arousal state of the cortex.

In some cases, stimulation of the second portion of brain 14, which may be more posterior to the first portion of brain 14, may improve communication within brain 14 (e.g., traversal of bioelectrical brain signals) within specific frequency bands of a bioelectrical brain signal. In one example, stimulation of the second portion of brain 14 may improve gamma band frequency communication within brain 14, which may increase an arousal state of patient 12 in a first, more frontal portion of brain 14. Different frequency bands are associated with different activity in brain 28. One example of the frequency bands is shown in Table 1:

TABLE 1

| Frequency (f) Band Hertz (Hz) | Frequency Information |
| --- | --- |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

Slowing of bioelectrical brain signals in some patients with Alzheimer's disease may interfere with normal, high frequency oscillations within brain 14 that may be observed in patients without Alzheimer's disease. In addition, the slowing of bioelectrical brain signals may disrupt frequency matching of oscillations of the bioelectrical brain signal across brain areas, which may interfere with communication of signals across brain 14. Slowing of bioelectrical brain signals may also prohibit phase locking of oscillations needed for normal mental function. Delivering electrical stimulation to the second portion of brain 14 to activate an arousal network within a first portion of brain 14, as described herein, may help improve communication across regions of brain 14 by improving the frequency matching of oscillations of the bioelectrical brain signal across brain areas and/or by improving the phase locking of oscillations of bioelectrical brain signals in different regions of brain 14.

Although leads 20 are shown in FIG. 1 as being coupled to a common lead extension 18, in other examples, leads 20 may be coupled to IMD 16 via separate lead extensions. In yet other examples, leads 20 may be directly coupled to IMD 16. In addition, although FIG. 1 illustrates system 10 as including two leads 20A and 20B coupled to IMD 16 via lead extension 18, in some examples, system 10 may include one lead or more than two leads.

Leads 20 may deliver electrical stimulation to treat any number of neurological disorders or diseases in addition to cognitive disorders, such as seizure disorders, movement disorders, or psychiatric disorders. Examples of movement disorders include a reduction in muscle control, motion impairment, or other movement problems, such as rigidity, bradykinesia, rhythmic hyperkinesia, nonrhythmic hyperkinesia, dystonia, tremor, and akinesia. Movement disorders may be associated with patient disease states, such as Parkinson's disease or Huntington's disease. Examples of psychiatric disorders include MDD, bipolar disorder, anxiety disorders, post traumatic stress disorder, dysthymic disorder, and OCD. As described above, examples of the disclosure are primarily described with regard to treating a cognitive disorder (e.g., Alzheimer's disease). Treatment of other patient disorders via delivery of therapy to brain 14 is contemplated.

Leads 20 may be implanted within a desired location of brain 14 via any suitable technique, such as through respective burr holes in a skull of patient 12 or through a common burr hole in the cranium 32. Leads 20 may be placed at any location within brain 14 such that electrodes 24, 26 of leads 20 are capable of providing electrical stimulation to targeted tissue during treatment. Electrical stimulation generated from the stimulation generator (not shown in FIG. 1) within the therapy module of IMD 16 may help treat (e.g., mitigate symptoms or improve the patient condition) associated with the patient's disorder. For example, in treatment of cognitive disorders such as Alzheimer's disease, electrical stimulation delivered to a target tissue site within brain 14 can help improve basic cognitive functions, e.g., memory processing, perception, problem solving, and language, that may be negatively affected by the cognitive disorder. In the examples described herein, electrical stimulation generated by the stimulation generator and delivered to a target portion of brain 14 can activate an arousal neural network in a portion of brain 14 to induce a desirable arousal state in brain 14. In some examples, the electrical stimulation delivered to brain 14 may induce a relatively high arousal state in brain 14 (e.g., as characterized by a relatively high amount of electrical activity sensed in a portion of brain 14), in comparison to a relatively low arousal state of brain 14 that may exist before delivery of electrical stimulation (e.g., as characterized by a relatively low amount of electrical activity sensed in the portion of brain 14). A relatively high arousal state in brain 14 may result in improved cognitive functions because patient 12 may be more engaged with, attentive to, and/or vigilant with respect to the surrounding environment and stimuli.

The particular parameter values that define the electrical stimulation that activates an arousal neural network in brain 14 of patient 12 in order to treat a cognitive disorder of patient 12 (e.g., the amplitude or magnitude of the stimulation signals, the duration of each signal, the waveform of the stimuli, e.g., rectangular, sinusoidal or ramped signals, the frequency of the signals, and the like) may be specific for the particular target stimulation site (e.g., the portion of brain 14 to which electrical stimulation therapy is delivered). In addition, the particular parameter values may be specific to the particular patient and to the particular patient disorder. In some examples, electrical stimulation defined by a relatively high frequency (e.g., electrical stimulation delivered at a frequency of greater than approximately 50-100 Hertz) delivered to areas of brain 28 associated with Alzheimer's disease related cognitive or memory dysfunction may effectively activate an arousal neural network in brain 14 of patient 12.

In some examples, a processor of therapy system 10 (e.g., a processor of programmer 22 or IMD 16) controls delivery of electrical stimulation by activating electrical stimulation, deactivating electrical stimulation, increasing the intensity of electrical stimulation, or decreasing the intensity of electrical stimulation delivered to brain 14 based on the arousal state of brain 14. In addition, in some examples, therapy system 10 may select a target tissue site (e.g., a target structure within brain 14) for the electrical stimulation based on the arousal state of brain 14.

Therapy system 10 may also store a plurality of stimulation programs (e.g., a set of electrical stimulation parameter values), and at least one stimulation program may be associated with at least one arousal state of brain 14. A processor of IMD 16 or programmer 22 may select a stored stimulation program that defines electrical stimulation parameter values for delivery of electrical stimulation to brain 14 based on a determined arousal state of brain 14. Where IMD 16 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. In some examples, at least one of the stored stimulation programs is associated with a respective one of at least two different arousal states. In addition, in some examples, at least one of the stored stimulation programs is associated with at least two different arousal states.

In some examples, therapy system 10 may be used in a trial stage to determine particular parameters of electrical stimulation that may be effective for inducing arousal in brain 14 of patient 12. That is, in some examples, therapy system 10 may be used to test various parameters of electrical stimulation delivered to patient 12 to determine the effectiveness of different stimulation programs and to identify stimulation parameters that are most effective in treating patient 12. In some examples, testing of stimulation parameters may be performed prior to implantation of IMD 16 in order to ensure that therapy delivered via IMD 16 will be effective in treating the cognitive disorder of patient 12.

During the trial stage, a plurality of stimulation programs may be tested and evaluated for efficacy in inducing one or more arousal states in brain 14. Stimulation programs may be selected for storage within IMD 16 based on the results of the trial stage. Therefore, the trial stage may be useful for customizing the therapy parameter values stored and implemented by IMD 16 for a particular patient 12.

In addition to delivering therapy to manage a disorder of patient 12, therapy system 10 monitors one or more bioelectrical brain signals of patient 12. For example, IMD 16 may include a sensing module (e.g., sensing module 44 of FIG. 2) that senses bioelectrical brain signals within one or more regions of brain 14. In the example shown in FIG. 1, the signals sensed by electrodes 24, 26 are conducted to the sensing module within IMD 16 via conductors within the respective lead 20A, 20B. As described in further detail below, in some examples, a processor of IMD 16 or another device (e.g., programmer 22) monitors the bioelectrical signals within brain 14 of patient 12 and controls delivery of electrical stimulation therapy to brain 14 based on the monitored bioelectrical brain signals to provide therapy to patient 12 in a manner that effectively treats a cognitive disorder of patient 12.

In some examples, the sensing module of IMD 16 may receive the bioelectrical signals from electrodes 24, 26 or other electrodes positioned to monitor bioelectrical brain signals of patient 12 (e.g., if housing 32 of IMD 16 is implanted in brain 14, an electrode of housing 32 can be used to sense bioelectrical brain signals and/or deliver stimulation to brain 14). Electrodes 24, 26 may also be used to deliver electrical stimulation from the therapy module to target sites within brain 14 as well as to sense brain signals within brain 14. However, IMD 16 can also use separate sensing electrodes to sense the bioelectrical brain signals. In some examples, the sensing module of IMD 16 may sense bioelectrical brain signals via one or more of the electrodes 24, 26 that are also used to deliver electrical stimulation to brain 14. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor brain signals and deliver electrical stimulation to the same region of brain 14 or to different regions of brain 14. In some examples, the electrodes used to sense bioelectrical brain signals may be located on the same lead used to deliver electrical stimulation while, in other examples, the electrodes used to sense bioelectrical brain signals may be located on a different lead than the electrodes used to deliver electrical stimulation. In some examples, a brain signal of patient 12 may be monitored with external electrodes, e.g., scalp electrodes. Moreover, in some examples, the sensing module that senses bioelectrical brain signals of brain 14 (e.g., the sensing module that generates an electrical signal indicative of the activity within brain 14) may be positioned in a physically separate housing from outer housing 32 of IMD 16. However, in the example shown in FIG. 1 and the example primarily referred to herein for ease of description, the sensing module and therapy module of IMD 16 are enclosed within a common outer housing 32. Other sensing and stimulation electrode configurations than those described above may also be used.

The bioelectrical brain signals monitored by IMD 16 may reflect changes in electrical current produced by the sum of electrical potential differences across brain tissue. Examples of the monitored bioelectrical brain signals include, but are not limited to, an electroencephalogram (EEG) signal, an electrocorticogram (ECoG) signal, a local field potential (LFP) sensed from within one or more regions of brain 14, and/or action potentials from single cells within the brain 14. As described in further detail below, therapy system 10 may control delivery of therapy to brain 14 of patient 12 based on the monitored brain signals of patient 12.

In some examples described herein, the monitored brain signals of patient 12 may be used to characterize the arousal state of brain 14. Example characteristics of the brain signals that may characterize the arousal state of brain 14 can include time domain characteristics (e.g., an amplitude or frequency) or frequency domain characteristics (e.g., an energy level in one or more frequency bands) of the brain signals sensed by IMD 16 within one or more regions of brain 14. For example, the characteristic of the brain signals may include an absolute amplitude value or a root mean square amplitude value. In addition, the amplitude value may comprise an average, peak, mean or instantaneous amplitude value over a period of time or a maximum amplitude or an amplitude in a particular percentile of the maximum (e.g., an amplitude value that represents 95% of the maximum amplitude value).

As another example, the characteristic of the brain signal may include the frequency, amplitude, and phase of the bioelectrical brain signal sensed within one or more regions of brain 14 of patient 12. The frequency, amplitude, and phase of the bioelectrical brain signal may indicate the oscillations in the brain signal. The oscillations in the sensed bioelectrical brain signal may represent the rhythmic or repetitive neural activity in brain 14. The neural oscillations may be determined based on one or more frequency domain characteristics of the bioelectrical brain signal.

In some examples, as illustrated in FIG. 1, therapy system 10 may also include sensor 28. In addition to electrodes 24, 26, sensor 28 can also measure a physiological response of patient 12 that can be indicative of a particular arousal state of brain 14. For example, sensor 28 may be configured to measure physiological parameters such as galvanic skin response, respiratory rate, heart rate, body temperature, and/or muscle activity of patient 12, and transmit the measurements to IMD 16 or another component of therapy system 10 to determine whether brain 14 is in a particular arousal state. Other physiological responses are also contemplated. As discussed above, in some examples, sensor 28 may be external to patient 12 and may communicate with IMD 16 and/or programmer 22 via a wireless communication link. In other examples, sensor 28 may be implanted within patient 12 and may communicate with IMD 16 via a wired or wireless communication link, and communicate with programmer 22 via a wireless communication link. In examples in which sensor 28 is implanted in patient 14, sensor 28 may be physically separate from IMD 16 or may be incorporated in IMD 16.

External programmer 22 wirelessly communicates with IMD 16 as needed to provide or retrieve therapy information. Programmer 22 is an external computing device that the user, e.g., the clinician and/or patient 12 or patient caretaker, may use to communicate with IMD 16. For example, programmer 22 may be a clinician programmer that the clinician uses to communicate with IMD 16 and program one or more therapy programs for IMD 16. Additionally or alternatively, programmer 22 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16.

Programmer 22 may be a hand-held computing device with a display viewable by the user and an interface for providing input to programmer 22 (i.e., a user input mechanism). For example, programmer 22 may include a small display screen (e.g., a liquid crystal display (LCD) or a light emitting diode (LED) display) that presents information to the user. In addition, programmer 22 may include a touch screen display, keypad, buttons, a peripheral pointing device or another input mechanism that allows the user to navigate though the user interface of programmer 22 and provide input. If programmer 22 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 22 may be a touch screen that allows the user to provide input directly to the user interface shown on the display. The user may use a stylus or their finger to provide input to the display.

In other examples, programmer 22 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 22. A wireless adapter coupled to the computing device may enable secure communication between the computing device and IMD 16.

When programmer 22 is configured for use by the clinician, programmer 22 may be used to transmit initial programming information to IMD 16. This initial information may include hardware information, such as the type of leads 20, the arrangement of electrodes 24, 26 on leads 20, the position of leads 20 within brain 14, initial programs defining therapy parameter values, and any other information that may be useful for programming into IMD 16. Programmer 22 may also be capable of completing functional tests (e.g., measuring the impedance of electrodes 24, 26 of leads 20).

The clinician may also store therapy programs within IMD 16 with the aid of programmer 22. During a programming session, the clinician may determine one or more stimulation programs that may effectively induce an arousal state in brain 14 of patient 12. For example, the clinician may select one or more electrode combinations with which stimulation is delivered to brain 14 to generate the arousal state. During the programming session, the clinician may evaluate the efficacy of the one or more electrode combinations based on one or more physiological parameters of patient 12 (e.g., heart rate, respiratory rate, galvanic skin response, bioelectrical brain signals, etc.). In some examples, programmer 22 may assist the clinician in the creation/identification of stimulation programs by providing a methodical system for identifying potentially beneficial stimulation parameter values. In some examples, the processor of programmer 22 may calculate and display one or more therapy metrics for evaluating and comparing therapy programs available to delivery of therapy from IMD 16 to patient.

The clinician may also program one or more physiological parameters with which IMD 16 may use to detect certain brain states of patient 12 used in controlling therapy delivery or monitoring patient 12. For example, the clinician may select one or more signal characteristics (e.g., a time domain or frequency domain characteristic) that indicate a portion of brain 28 associated with one or more symptoms of Alzheimer's disease is in a relatively low arousal state.

Programmer 22 may also be configured for use by patient 12. When configured as a patient programmer, programmer 22 may have limited functionality (compared to a clinician programmer) in order to prevent patient 12 from altering critical functions of IMD 16 or applications that may be detrimental to patient 12. In this manner, programmer 22 may only allow patient 12 to adjust values for certain therapy parameters or set an available range of values for a particular therapy parameter.

Programmer 22 may also provide an indication to patient 12 when therapy is being delivered, when patient input has triggered a change in therapy or when the power source within programmer 22 or IMD 16 needs to be replaced or recharged. For example, programmer 22 may include an alert LED, may flash a message to patient 12 via a programmer display, generate an audible sound or somatosensory cue to confirm patient input was received, e.g., to indicate a patient state or to manually modify a stimulation parameter.

Whether programmer 22 is configured for clinician or patient use, programmer 22 is configured to communicate with IMD 16 and, optionally, another computing device, via wireless communication. Programmer 22, for example, may communicate via wireless communication with IMD 16 using radio frequency (RF) telemetry techniques known in the art. Programmer 22 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 22 may also communicate with other programming or computing devices via exchange of removable media, such as magnetic or optical disks, memory cards or memory sticks. Further, programmer 22 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
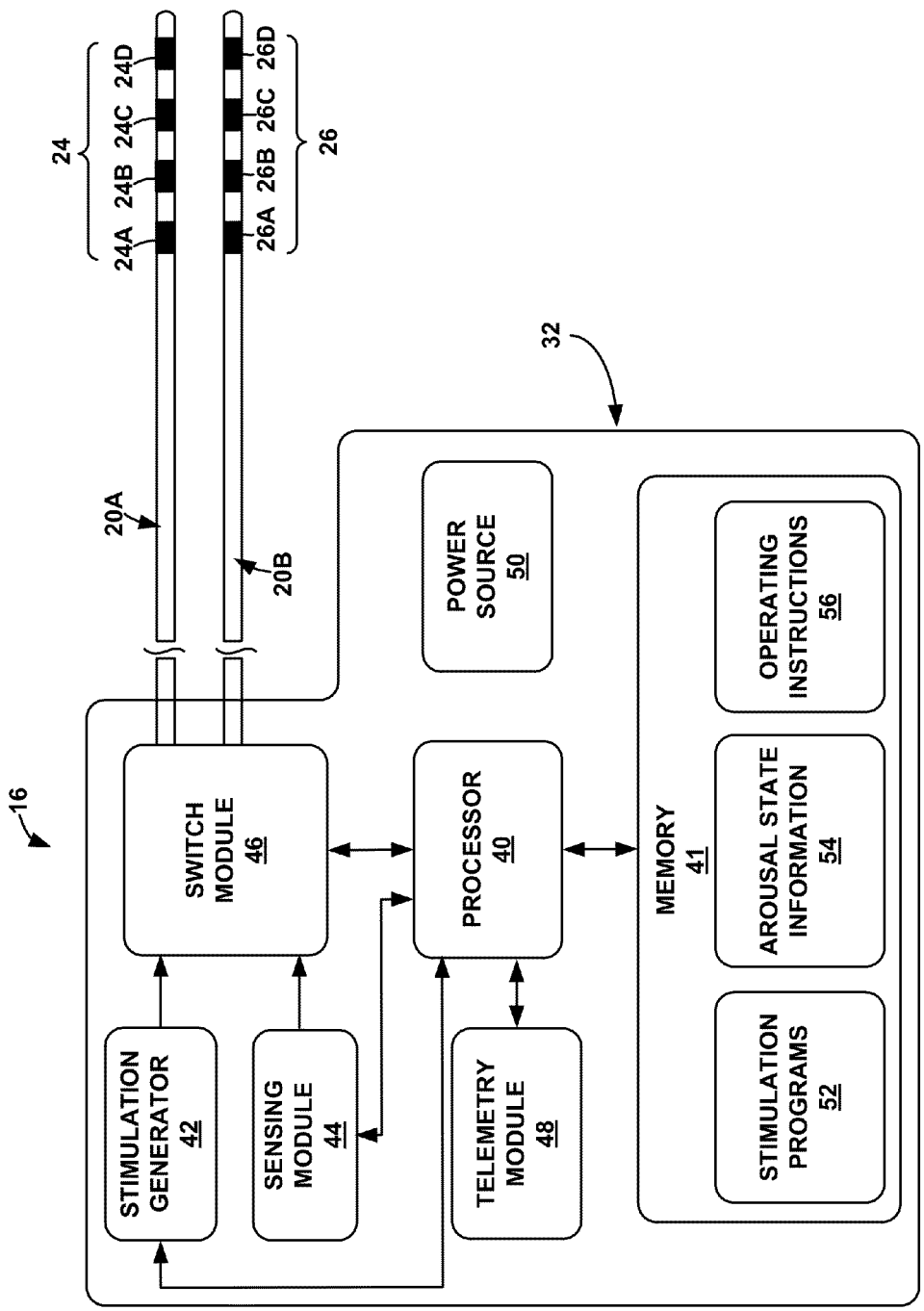
FIG. 2 is a functional block diagram illustrating components of an implantable medical device of the therapy system illustrated in FIG. 1.

FIG. 2 is a functional block diagram illustrating components of IMD 16. In the example shown in FIG. 2, IMD 16 includes processor 40, memory 41, stimulation generator 42, sensing module 44, switch module 46, telemetry module 48, and power source 50. Memory 41 may include any volatile or non-volatile media, such as a random access memory (RAM), read only memory (ROM), non-volatile RAM (NVRAM), electrically erasable programmable ROM (EEPROM), flash memory, and the like. Memory 41 may store computer-readable instructions that, when executed by processor 40, cause IMD 16 to perform various functions described herein.

In the example shown in FIG. 2, memory 41 stores stimulation programs 52, arousal state information 54, and operating instructions 56 in separate memories within memory 41, or in separate modules within memory 41. Each stored stimulation program 52 (which can also be referred to as a type of therapy program) defines a particular set of electrical stimulation parameters, e.g., a stimulation electrode combination, electrode polarity, frequency, current or voltage amplitude. In examples in which stimulation generator 42 generates and delivers stimulation pulses, the stimulation programs 52 may define values for pulse width and pulse rate of the stimulation signal. In some examples, one or more of the stimulation programs 52 may be stored as a therapy group, e.g., a group of related stimulation programs. The stimulation signals defined by the stimulation programs of the therapy group may be delivered together on an overlapping or non-overlapping (e.g., time-interleaved) basis. In addition, memory 41 may store information related to a schedule according to which electrical stimulation is delivered to brain 14 (e.g., a schedule defining a total amount of time daily that stimulation is delivered to brain 14, a schedule defining particular points in time during which stimulation is delivered, a schedule defining a cyclical basis on which stimulation is delivered, and the like).

In the example illustrated in FIG. 2, memory 41 also stores arousal state information 54. Arousal state information 54 may include information related to one or more arousal states of brain 14 of patient 12. For example, in some examples, arousal state information 62 may include signal characteristics that identify a bioelectrical brain signal representative of a particular arousal state of brain 14 (e.g., a particular anatomical structure or region of brain 14). That is, arousal state information 62 may store signal characteristics that are biomarkers for a particular arousal state of brain 14. Arousal state information may be specific to patient 14 or may be more general (e.g., based on data from a group of patients, which may or may not include patient 14) and applied to patient 14. In some cases, when IMD 16 is used to deliver electrical stimulation to manage Alzheimer's disease, the information (e.g., threshold values) indicative of a relatively high arousal state may be based on a patient or a group of patients without Alzheimer's disease or otherwise without reduced cognitive function. In this way, the electrical stimulation may seek to increase the patient's arousal state to above some nominal state and to an arousal state that is also observed in patients without Alzheimer's disease.

As an example of arousal state information, as discussed above, in some examples, a bioelectrical brain signal indicative of a relatively high arousal state in brain 14 may be defined by a bioelectrical brain signal exhibiting relatively small amplitude values and relatively high frequency values compared to a bioelectrical brain signal indicative of a relatively low arousal state in brain 14. Consequently, in some examples, arousal state information 54 may include predefined threshold values for amplitude and/or frequency of a bioelectrical brain signal that correlate to a relatively high arousal state and/or to a relatively low arousal state in brain 14.

In some examples, processor 40 may compare characteristics of a bioelectrical brain signal to the threshold values stored as arousal state information 54 in order to detect a relatively low arousal state of brain 14 or a relatively high arousal state of brain 14. As an example of a signal processing technique that processor 50 may employ to determine whether a sensed bioelectrical brain signal includes a biomarker for a particular arousal state (e.g., an arousal state that activates the delivery of therapy), processor 40 may analyze a sensed bioelectrical signal amplitude of frequency correlation with a template signal, or a specific stored value. For example, the instantaneous, peak, lowest or average amplitude of the bioelectrical brain signal over a period of time (which can be predetermined) may be compared to an amplitude threshold. In one example, as described below, when the amplitude of the bioelectrical brain signal sensed within a first portion of brain 14 is greater than or equal to the threshold value, processor 40 may control stimulation generator 42 to deliver stimulation to a second portion of brain 14.

As another example, arousal state information 54 may store portions of bioelectrical brain signals (e.g., waveforms or specific values of signal characteristics) previously sensed within brain 14 of patient 14 that correspond to a particular arousal state of brain 14. In some examples, the stored bioelectrical brain signals can be used as a template to determine whether a particular sensed bioelectrical brain signal is indicative of a particular arousal state of brain 14. As an example of a signal processing technique that processor 40 may employ to determine whether the bioelectrical brain signal includes the biomarker associated with a particular arousal state, processor 40 may analyze the bioelectrical brain signal with temporal correlation or frequency correlation with a template signal, or combinations thereof. As another example, a slope of the amplitude of the bioelectrical brain signal over time or timing between inflection points or other critical points in the pattern of the amplitude of the bioelectrical brain signal over time may be compared to trend information stored by arousal state information 54. A correlation between the inflection points in the amplitude waveform of the bioelectrical brain signal or other critical points and a template may indicate the bioelectrical brain signal includes the biomarker indicative of the arousal state associated with the template. Processor 40 may implement an algorithm that recognizes a trend of the bioelectrical brain signal that characterizes the biosignal. As described in further detail below, if the trend of the bioelectrical brain signal matches or substantially matches the trend template, processor 40 may control stimulation generator 42 to deliver stimulation to a second portion of brain 14 of patient 12.

As another example, processor 40 may perform temporal correlation by sampling the waveform generated by a sensed bioelectrical brain signal with a sliding window and comparing the waveform with a template waveform stored by arousal state information 54 that is associated with a particular arousal state (e.g., a relative high arousal state or a relatively low arousal state). For example, processor 60 may perform a correlation analysis by moving a window along a digitized plot of the amplitude waveform of a sensed bioelectrical brain signal at regular intervals, such as between about one millisecond to about ten millisecond intervals, to define a sample of the bioelectrical brain signal. The sample window is slid along the plot until a correlation is detected between the waveform of the template and the waveform of the sample of the brain signal defined by the window. By moving the window at regular time intervals, multiple sample periods are defined. The correlation may be detected by, for example, matching multiple points between the template waveform and the waveform of the plot of the sensed bioelectrical brain signal over time, or by applying any suitable mathematical correlation algorithm between the sample in the sampling window and a corresponding set of samples stored in the template waveform.

As described below with respect to FIGS. 6A-6C, processor 40 may implement techniques other than those described above to detect an arousal state of patient 12. For example, as described with respect to FIG. 6A, processor 40 may detect desynchronization of bioelectrical brain signals within a first portion of brain 14. As another example, as described with respect to FIG. 6B, processor 40 may detect, based on a sensed bioelectrical brain signal, a widespread activation of an arousal network of brain 14, which may indicate the first portion of brain 14 is in a relatively high arousal state. As another example, as described with respect to FIG. 6C, processor 40 may detect an arousal state of patient based on a physiological parameter of patient 12 other than a bioelectrical brain signal, where a particular value or other characteristic of the physiological parameter may be associated with a specific arousal state. The value or other characteristic of the physiological parameter that is associated with a specific arousal state may be stored as arousal state information 54 or within a memory of another device.

Stimulation generator 42, under the control of processor 40, generates stimulation signals for delivery to patient 12 via selected combinations of electrodes 24, 26. Processor 40 controls stimulation generator 42 according to stimulation programs 52 stored in memory 41 to apply particular stimulation parameter values specified by one or more programs, such as amplitude, pulse width, and pulse rate. In some examples, stimulation generator 42 generates and delivers stimulation signals to one or more target portions (e.g., "second" portions) of brain 14, e.g., Basal Nucleus of Meynert, anterior cingulate gyms, ascending reticular activation system, via a select combination of electrodes 24, 26, where the stimulation signals have a frequency in a range of about 50 Hertz (Hz) to about 250 Hz, a voltage of about 0.1 volts to about 10.5 volts, and a pulse width of about 60 microseconds to about 450 microseconds. In some examples, the stimulation signals have a frequency of 130 Hz, a voltage of about 2 volts, and a pulse width of about 60 microseconds. In addition, in some examples, the stimulation signals have a frequency of 145 Hz, a voltage of about 5 volts, and a pulse width of about 145 microseconds.

Other stimulation parameter values may also be used and may vary depending on the patient and the patient's response to the stimulation. For example, some patients may require a higher intensity (e.g., a function of a plurality of stimulation parameter values, such as the frequency, amplitude, and pulse width) stimulation delivered to a second portion of brain 14 to cause a first portion of brain 14 to transition from a relatively low arousal state to a relatively high arousal state that provides observable (e.g., by patient 12, patient caretaker or clinician) changes in the patient's Alzheimer state. As another example, depending on the structure of brain 14 that is being activated by the stimulation, a lower frequency stimulation may be desirable, such as a frequency of about 50 Hz or less, in order to activate certain structures.

Various target tissue sites within brain 14, stimulation parameter values, and other therapy delivery schedules are contemplated. In some examples, other ranges of stimulation parameter values may also be useful, and may be determined based on the target stimulation site within patient 12, which may or may not be within brain 14. While stimulation pulses are described, stimulation signals may be of any form, such as continuous-time signals (e.g., sine waves) or the like.

In each of the examples described herein, if stimulation generator 42 shifts the delivery of stimulation energy between two stimulation programs and/or two different electrode combinations, processor 40 of IMD 16 may provide instructions that cause stimulation generator 42 to time-interleave stimulation energy between the electrode combinations of the two therapy programs, e.g., using the technique described in commonly-assigned U.S. Pat. No. 7,519,431, entitled, "SHIFTING BETWEEN ELECTRODE COMBINATIONS IN ELECTRICAL STIMULATION DEVICE," which issued on Apr. 14, 2009, the entire content of which is incorporated herein by reference. In the time-interleaved shifting example, the amplitudes of the stimulation signals delivered via the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs and/or electrode combinations may be used in other examples.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40, as well as processors described herein, may be embodied as firmware, hardware, software or any combination thereof.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 40 may control switch module 46 to apply the stimulation signals generated by stimulation generator 42 to selected combinations of electrodes 24, 26. In particular, switch module 46 may couple stimulation signals to selected conductors within leads 20, which, in turn, deliver the stimulation signals across selected electrodes 24, 26. Switch module 46 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 42 is coupled to electrodes 24, 26 via switch module 46 and conductors within leads 20. In some examples, however, IMD 16 does not include switch module 46.

Stimulation generator 42 may be a single channel or multi-channel stimulation generator. In particular, stimulation generator 42 may be capable of delivering a single stimulation pulse, multiple stimulation pulses, or a continuous signal at a given time via a single electrode combination or multiple stimulation pulses at a given time via multiple electrode combinations. In some examples, however, stimulation generator 42 and switch module 46 may be configured to deliver multiple channels on a time-interleaved basis. For example, switch module 46 may serve to time divide the output of stimulation generator 42 across different electrode combinations at different times to deliver multiple programs or channels of stimulation energy to patient 12.

Sensing module 44 is configured to sense bioelectrical brain signals of patient 12 via a selected subset of electrodes 24, 26, or with one or more electrodes 24, 26 and at least a portion of a conductive outer housing 32 of IMD 16, an electrode on an outer housing of IMD 16, or another reference. Processor 40 may control switch module 46 to electrically connect sensing module 44 to selected electrodes 24, 26. In this way, sensing module 44 may selectively sense bioelectrical brain signals with different combinations of electrodes 24, 26 (and/or a reference other than an electrode 24, 26). As described above, with arousal state information 54 that is stored by IMD 16 (or another device in other examples), processor 40 may monitor the sensed bioelectrical brain signals to monitor and determine the arousal state of brain 14 (e.g., by detecting a specific arousal state of patient 14).

In some examples, a bioelectrical brain signal that exhibits a frequency in a gamma band, such as about 50 Hz to about 100 Hz, or about 50 Hz to about 85 Hz, such as about 70 Hz may be indicative of a relatively high arousal state in which the cognitive function of patient 12 is improved. In addition, in some examples, a bioelectrical brain signal that exhibits a frequency in a beta band, such as about 10 Hz to about 30 Hz, such as about 16 Hz to about 30 Hz may be indicative of a relatively high arousal state in which the cognitive function of patient 12 is improved. In some cases, the relatively high frequency activity of the bioelectrical brain signal that is indicative of the relatively high arousal state of patient 12 may be determined based on a time domain bioelectrical brain signal or a frequency domain bioelectrical brain signal, such as the power level within a particular frequency band. In some cases, an increase in activity in the gamma band and/or the beta band may be indicative of a relatively high arousal state, e.g., that the therapy delivery to the second portion of brain 14 has increased the arousal state of the first portion of brain 14.

In some examples, a bioelectrical brain signal that exhibits a frequency in a theta band, such as about 5 Hz to about 7 Hz may be indicative of a relatively low arousal state, such that therapy delivery to increase the arousal state may be desirable. In some cases, an increase in activity in the theta band may be indicative of a relatively low arousal state.

Further, in some cases, the ratio of beta band and/or gamma band activity to the theta band activity may be used to determine the arousal state of the first portion of brain 14. The ratio value that indicates that the beta band and/or gamma band activity is relatively high relative to the theta band activity may indicate the relatively high arousal state. In addition, the ratio value that indicates the beta band and/or gamma band activity is relatively low relative to the theta band activity (or that the theta band activity is relatively high relative to the beta band and/or gamma band activity) may indicate the first portion of brain 14 is in a relatively low arousal state, such that therapy delivery to increase the arousal state may be desirable.

In some examples, processor 40 may monitor a bioelectrical brain signal sensed in a first portion of brain 14 by sensing module 44 in order to acquire information about the arousal state of brain 14. For example, the first portion of brain 14 may include a previously-identified arousal neural network, e.g., a network of neural tracts (fibers) or neurons (cell bodies) that may be instrumental in effecting arousal in brain 14. Monitoring electrical activity in the first portion of brain 14 may provide information about the activity level of the arousal neural network. Based on the electrical activity within the first portion of brain 14, which may be indicative of the activity of the arousal neural network, IMD 16 can determine whether brain 14 is in a relatively low or relatively high arousal state. In some examples, a relatively low arousal state of brain 14 may be defined as a state of brain 14 in which particular arousal neural networks of brain 14 exhibit a reduced amount of electrical activity. A relatively low arousal state of brain 14 may result in lack of engagement of patient 12 with surrounding environment and stimuli. In contrast, in some examples, a relatively high arousal state of brain 14 may be defined as a state in which particular arousal neural networks of brain 14 exhibit an increased amount of electrical activity. A relatively high arousal state of brain 14 may indicate that patient 12 is relatively more alert, vigilant, and responsive to stimuli, in comparison to a relatively low arousal state of brain 14.

As discussed above, the information stored as arousal state information 54 that is indicative of the relatively low arousal state of the first portion of brain 14 may be specific to patient 14 or may be more general. In examples in which the biomarkers indicative of the low arousal state of the first portion of brain 14 are specific to patient 14, a clinician may determine the biomarkers using any suitable technique. In one example, the clinician determines when patient 12 exhibits one or more symptoms of Alzheimer's disease (e.g., confusion, irritability, short-term or long-term memory loss) and determines the bioelectrical brain signal sensed by IMD 16 or another device (e.g., a temporary monitoring device) that correlates in time to when patient 12 exhibited the one or more symptoms of Alzheimer's disease. The exhibition of one or more symptoms of Alzheimer's disease may be referred to as an Alzheimer's disease episode, where each episode may be associated with the exhibition of one or more symptoms. Episodes that occur in a short range of time (e.g., within less than an hour or otherwise determined by the clinician) may be clustered together to define a common episode. The clinician may determine when patient 12 exhibits one or more symptoms of Alzheimer's based on any suitable and reliable information, such as by observing patient 12 in the clinic or based on a diary or the like kept by a patient caretaker, where the diary catalogs the times at which patient 12 exhibited an Alzheimer's disease episode symptoms and, in some cases, the severity of the episode.

Processor 40 of IMD 16 or a processor of another device, such as programmer 24, may determine the or more biomarkers indicative of the relatively low arousal state based on the bioelectrical brain signal that temporally correlates to the Alzheimer's disease episode. The biomarkers may be selected by the clinician or automatically by a processor, and may be selected as the signal characteristics that distinguish the bioelectrical brain signal sensed during an Alzheimer's disease episode from a bioelectrical brain signal sensed at other times.

In examples in which the biomarkers indicative of the low arousal state of the first portion of brain 14 are not specific to patient 14, but are based on a group of patients that may or may not include patient 14, the biomarkers may be determined using similar techniques as that described above for determining the biomarkers based on information specific to patient 14. The biomarkers can be, for example, a threshold that represents the average bioelectrical brain signal amplitude that is indicative of a relatively low arousal state. Other types of biomarkers that are generated based on a patient other than patient 14 and/or a plurality of patients are contemplated.

In some examples, a relatively low arousal state of brain 14 may be characterized by pathological synchronization of electrical activity within across areas of brain 14, e.g., two or more regions of a common arousal neural network. That is, in some examples, the bioelectrical brain signals exhibited throughout a portion of brain 14 that includes an arousal neural network may be synchronized and be defined by similar characteristics, e.g., similar amplitudes, frequencies, and the like. In some examples, the synchronization may be indicative of brain 14 "falling into a rut." For example, in some examples, the synchronization may be indicative of routine activity within brain 14 that causes brain 14 to be less reactive to and functional in processing stimuli.

In addition to causing synchronization within brain 14, in some examples, a relatively low arousal state of brain 14 may result in bioelectrical brain signals defined by relatively higher amplitudes and relatively lower frequencies, in comparison to bioelectrical brain signals of brain 14 in a relatively high arousal state. When brain 14 is in a relatively high arousal state, different areas of brain 14 may be activated and then subsequently desynchronized, e.g., there may be an increase in activity in relatively high frequency bands (e.g., the beta or gamma bands). Thus, when IMD 16 delivers stimulation to the second portion of brain 14 to increase an arousal state of a first portion of brain 14, the stimulation may desynchronize low frequency activity (e.g., around 7 Hz or less) in the first portion of brain 14, such that the frequency of the brain signal sensed in the first portion of brain 14 increases.

The low frequency activity may be indicative of synchronization and of a non-aroused brain state or a relatively low arousal state. Low frequency activity may capture a larger portion of brain 14 and inhibit brain 14 from functioning at a higher arousal state. Consequently, if sensing module 44 senses one or more bioelectrical brain signals defined by synchronization, relatively higher amplitudes, and/or relatively lower frequencies, processor 40 may determine that brain 14 is in a relatively low arousal state. These types of bioelectrical brain signals may be detected based on information stored by arousal state information 54 of memory 41 or stored by a memory of another device.

In contrast, in some examples, a relatively high arousal state of brain 14 may be characterized by desynchronization within a portion of brain 14 that includes an arousal neural network. Desynchronization within brain 14 may be characterized by a bioelectrical brain signal that exhibits relatively smaller amplitudes and relatively higher frequencies (e.g., high frequency oscillations), which sometimes exhibits chaotic electrical activity, in comparison to bioelectrical brain signals of brain 14 in a relatively low arousal state. Examples of the relatively higher frequencies indicative of desynchronization include the gamma band and beta band ranges (see Table 1 above). It is believed that this relatively high frequency activity is indicative of more independence of activity between brain regions, which may also result in a lower amplitude. Consequently, if sensing module 44 senses one or more bioelectrical brain signals defined by desynchronization, processor 40 may determine that brain 14 is in a relatively high arousal state. Again, these types of bioelectrical brain signals that are associated with a relatively high arousal state may be detected based on information stored by arousal state information 54 of memory 41 or stored by a memory of another device.

In some examples, in order to detect pathological synchronization across large areas of brain 14, e.g., including to or more portions of brain 14, processor 40 may monitor two or more bioelectrical brain signals sensed by sensing module 44 (e.g., via two or more electrodes 24, 26) in different regions of a portion of brain 14 that includes an arousal neural network. If processor 40 identifies synchronization between the two or more bioelectrical brain signals, e.g., the two or more bioelectrical brain signals are defined by similar frequencies, amplitudes, phases, and/or other signal characteristics, processor 40 may determine that brain 14 is in a relatively low arousal state. The synchronization across large areas of brain 14 may indicate that the electrical activity within brain 14 is prohibiting normal cognitive function. On the other hand, if processor 40 does no identify pathological synchronization between the two or more bioelectrical brain signals sensed by sensing module 44, e.g., the two or more bioelectrical brain signals are defined by differing frequencies, amplitudes, phases, and/or other signal characteristics, processor 40 may determine that brain 14 is in a relatively high arousal state.

In other examples, processor 40 may monitor bioelectrical brain signals sensed by sensing module 44 in another suitable manner in order to determine the arousal state of brain 14. For example, in some examples, sensing module 44 may directly sense a bioelectrical brain signal, e.g., a local field potential (LFP), via one or more of electrodes 24, 26 at a particular point within a portion of brain 14 that includes an arousal neural network, and processor 40 may monitor the bioelectrical brain signal. In some examples, processor 40 may compare one or more characteristics (e.g., amplitude or frequency) of the bioelectrical brain signal to a threshold value to determine whether brain 14 is in a particular arousal state, e.g., a relatively low arousal state or a relatively high arousal state. For example, arousal state information module 54 of memory 41 may store information related to threshold values for signal characteristics that define particular arousal states of brain 14, and processor 40 may compare characteristics of the sensed bioelectrical brain signals to the stored values.

As another example, therapy system 10 may include one or more external electrodes positioned on the outer surface of the cranium of patient 12 that can sense and generate a bioelectrical brain signal, e.g., an electroencephalogram (EEG) signal, that can be used to determine an arousal state of brain 14. For example, the external electrodes may generate a bioelectrical brain signal, transmit the bioelectrical brain signal to IMD 16 or another component of therapy system 10 (e.g., via wireless telemetry), and processor 40 or another component of therapy system 10 can determine whether activity within brain 14 is indicative of a particular arousal state of brain 14, e.g., a relatively low arousal state or a relatively high arousal state, based on characteristics of the bioelectrical brain signal. In some examples, bioelectrical brain signals generated by external electrodes may more accurately depict widespread, e.g., global, activation of neural networks in brain 14, in comparison to electrodes 24, 26 which are implanted within brain 14 and which may, in some examples, detect signals indicative of activity at one or more particular points within brain 14. In some examples, a widespread increase in electrical activity within brain 14 may be indicative of increased activation of an arousal neural network in brain 14 and, consequently, of an increased arousal state of brain 14, e.g., a relatively high arousal state.

Figure 3:
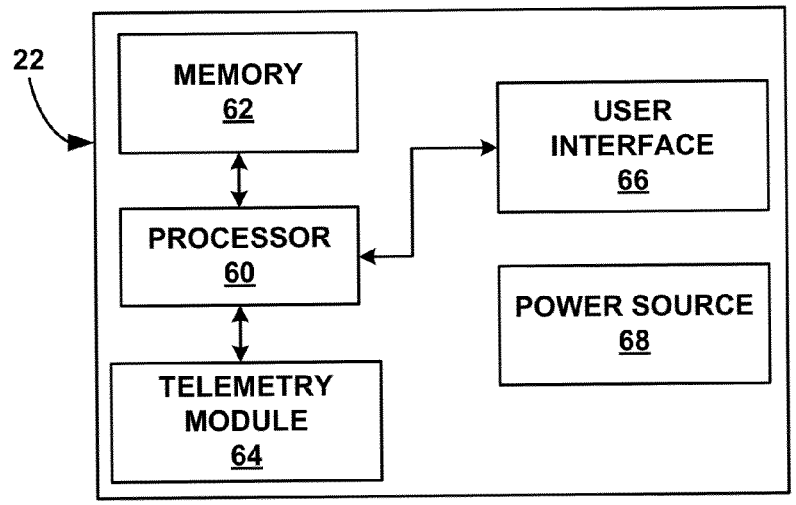
FIG. 3 is a functional block diagram illustrating components of an example external programmer of the therapy system illustrated in FIG. 1.

Although sensing module 44 is incorporated into a common housing 32 with stimulation generator 42 and processor 40 in FIG. 3, in other examples, sensing module 44 is in a physically separate outer housing from outer housing 32 of IMD 16 and communicates with processor 40 via wired or wireless communication techniques.

In some examples, as previously mentioned, therapy system 10 may also include a sensor 28, which can measure a physiological response of patient 12 to determine an arousal state of brain 14. For example, in some examples, sensor 28 that is external to patient 12 can measure a galvanic skin response of patient 12. The galvanic skin response of patient 12 is a measurement of the electrical conductance of the skin of patient 12, and may vary with the moisture level of the skin, e.g., as a result of sweating. In some examples, a relatively high arousal state in brain 14 can be characterized by increased moisture level of the skin, e.g., increased perspiration, of patient 12, which can result in increased galvanic skin response, e.g., electrical conductance of the skin, of patient 12. Consequently, an increased galvanic skin response of patient 12 may be indicative of increased state of arousal of brain 14.

In some examples, sensor 28 can transmit measurements of the physiological response to processor 40 of IMD 16, e.g., via wireless telemetry, and processor 40 can determine an arousal state of brain 14 based on the signal generated by sensor 28. Processor 40 can use any suitable technique for determining the arousal state of brain 14 based on physiological response measurements. For example, in some examples, processor 40 may compare a particular physiological response measurement to a previously acquired measurement to determine whether a change in the physiological response has occurred over time. If processor 40 identifies a change, processor 40 may determine that the arousal state of brain 14 has changed. In other examples, arousal state information module 54 of memory 41 may store particular physiological response measurement values and corresponding arousal states for patient 12, and processor 40 may compare a particular physiological response measurement received from external sensor 28 to the stored values to determine whether brain 14 is in a particular arousal state. Although the examples are described with respect to processor 40 determining the arousal state of brain 14, in other examples, another component of therapy system 10 can determine the arousal state of brain 14.

Based on determining the arousal state of brain 14, processor 40 may control stimulation generator 42 to deliver stimulation to brain 14 via one or more electrodes 24, 26 according to a specific therapy program, which can be associated with the determined arousal state. For example, processor 40 may determine that a different arousal state may be more desirable to address (e.g., terminate or mitigate the severity) an Alzheimer's disease episode or for the situation, environment, and/or surrounding stimuli to which patient 12 is currently exposed, and may deliver stimulation to induce the different arousal state. As an example, processor 40 may determine that brain 14 is in a relatively low arousal state but that a relatively high arousal state of brain 14 may be more desirable, e.g., for patient 12 to react to surrounding stimuli. Processor 40 may subsequently control stimulation generator 42 to deliver stimulation to a portion of brain 14 to activate an arousal neural network in order to induce a relatively high arousal state in brain 14.

As described above, in some examples, processor 40 may control stimulation generator 42 to deliver electrical stimulation to brain 14 to induce a particular arousal state when a different arousal state is detected. For example, if processor 40 may continually or periodically monitor a bioelectrical brain signal of patient 14 and determine the arousal state associated with the signal. If processor 40 determines that a sensed bioelectrical brain signal indicates a relatively low arousal state, processor 40 may control stimulation generator 42 to deliver electrical stimulation to brain 14 to induce a higher arousal state that results in observable (e.g., by a patient caretaker or clinician) improvement in the patient's Alzheimer's disease condition, such as a mitigation or termination of an Alzheimer's episode. In some examples in which electrical stimulation is delivered to a patient with Alzheimer's disease to increase the arousal of brain 14, the electrical stimulation is configured to induce an arousal state that is above some nominal state (e.g., above some nominally conscious state), such that the patient is better able to interact with the environment, retain memories, and process information.

In some examples, processor 40 may control stimulation generator 42 to deliver electrical stimulation to brain 14 to induce a particular arousal state only at particular points in time. For example, in some examples, a particular arousal state of brain 14 may be desirable for patient 12 only in particular situations, environments, and/or during particular events (e.g., when patient 12 wants to personally interact with others, when patient 12 wants to be cognitively engaged, during memory intensive times, when patient 12 is trying to memorize things, when task-related attention is required, and the like). In some examples, processor 40 may receive user input, e.g., via programmer 22, indicating that electrical stimulation of brain 14 to induce a particular arousal state in brain 14 is desirable. For example, a clinician or patient 12 may provide input, e.g., to programmer 22, indicating that patient 12 is in a situation in which patient 12 would benefit from a vigilant or attentive brain state. Upon receiving the user input, processor 40 may control stimulation generator 42 to deliver electrical stimulation to brain 14 to induce a relatively high arousal state in brain 14.

In other examples, processor 40 may control stimulation generator 42 to deliver electrical stimulation to brain 14 to induce a particular arousal state on a predetermined schedule. For example, a relatively high arousal state of brain 14 may be desirable during time periods in which patient 12 is awake and active, e.g., during the day, such that patient 12 can be attentive to and engaged in daily activities. Consequently, processor 40 may control stimulation generator 42 to deliver electrical stimulation to a target tissue site within brain 14 that includes an arousal neural network to induce arousal in brain 14 during time periods in which patient 12 is awake. In contrast, a relatively low arousal state of brain 14 may be more desirable during time periods in which patient 12 is asleep, e.g., at night, such that patient 12 can successfully maintain a sleeping state, e.g., to relax and rest. Consequently, in some examples, processor 40 may control stimulation generator 42 to terminate delivery of electrical stimulation or reduce the magnitude of electrical stimulation delivered when patient 12 is asleep in order to induce a relatively low arousal state of brain 14. Other schedules for delivery of electrical stimulation to induce a particular arousal state in brain 14 are contemplated.

Telemetry module 48 supports wireless communication between IMD 16 and an external programmer 22 or another computing device under the control of processor 40. Processor 40 of IMD 16 may receive, as updates to stimulation programs, values for various stimulation parameters such as amplitude and electrode combination, or arousal state information 54 from programmer 22 via telemetry module 48. The updates to the stimulation programs may be stored within stimulation programs 52 of memory 41. Telemetry module 48 in IMD 16, as well as telemetry modules in other devices and systems described herein, such as programmer 22, may accomplish communication by RF communication techniques. In addition, telemetry module 48 may communicate with external medical device programmer 22 via proximal inductive interaction of IMD 16 with programmer 22. Accordingly, telemetry module 48 may send information to external programmer 22 on a continuous basis, at periodic intervals, or upon request from IMD 16 or programmer 22. For example, processor 40 may transmit information stored in arousal state information 54 to programmer 22 via telemetry module 48.

Power source 50 delivers operating power to various components of IMD 16. Power source 50 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

FIG. 3 is a functional block diagram illustrating components of an example medical device programmer 22 (FIG. 1). Programmer 22 includes processor 60, memory 62, telemetry module 64, user interface 66, and power source 68. Processor 60 controls user interface 66 and telemetry module 64, and stores and retrieves information and instructions to and from memory 62. Programmer 22 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 22 through user interface 66. For example, a clinician may provide input via user interface 66 related to stimulation parameters that define stimulation effective in inducing an arousal state in brain 14, and programmer 22 may transmit the stimulation parameters to IMD 16. As another example, a clinician or another user may provide user input via user interface 66 related to situations in which a particular arousal state of brain 14 may be desirable, e.g., situations in which patient 12 may benefit from an increased state of arousal.

User interface 66 includes a display (not shown), such as a LCD or LED display or other type of screen, to present information related to the therapy, such as information related to bioelectrical brain signals sensed via a plurality of sense electrode combinations. In addition, user interface 66 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 22 and provide input.

If user interface 66 includes buttons and a keypad, the buttons may be dedicated to performing a certain function, i.e., a power button, or the buttons and the keypad may be soft keys that change function depending upon the section of the user interface currently viewed by the user. Alternatively, the display screen (not shown) of programmer 22 may be a touch screen that allows the user to provide input directly to the user interface shown on the display. The user may use a stylus or their finger to provide input to the display. In other examples, user interface 66 also includes audio circuitry for providing audible instructions or sounds to patient 12 and/or receiving voice commands from patient 12, which may be useful if patient 12 has limited motor functions. Patient 12, a clinician or another user may also interact with programmer 22 to manually select stimulation programs, generate new stimulation programs, modify stimulation programs through individual or global adjustments, and transmit the new programs to IMD 16.

In some examples, at least some of the control of electrical stimulation delivery by IMD 16 may be implemented by processor 60 of programmer 22. For example, processor 60 may perform any of the techniques described herein with respect to processor 40 of IMD 16. For example, in some examples, processor 60 may receive sensed brain signal information from IMD 16 or from a sensing module that is separate from IMD 16. The separate sensing module may, but need not be, implanted within patient 12. Brain signal information may include, for example, a time domain characteristic (e.g., an amplitude) or a frequency domain characteristic (e.g., an energy level in one or more frequency bands) of bioelectrical brain signals monitored by sensing module 44 using one or more of electrodes 24, 26 (FIG. 2). Based on the monitored brain signal information, processor 60 may determine an arousal state of brain 14 and control delivery of electrical stimulation from IMD 16 to patient 12 based on the determined arousal state. For example, processor 60 may determine that brain 14 is in a relatively low arousal state and that a relatively high arousal state may be more desirable for patient 12. Consequently, processor 60 may transmit a control signal that causes stimulation generator 42 of IMD 16 (FIG. 2) to deliver electrical stimulation to a portion of brain 14 previously determined to activate an arousal neural network within brain 14 to increase the arousal state of brain 14.

Memory 62 may include instructions for operating user interface 66 and telemetry module 64, and for managing power source 68. Memory 62 may also store any therapy data retrieved from IMD 16 during the course of therapy, stimulation programs, arousal state information, and information related to schedules according to which stimulation can be delivered to brain 14. The clinician may use this therapy data to determine stimulation parameters and treatment plans that can most effectively treat the cognitive disorder of patient 12. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 22 is used by a different patient.

Wireless telemetry in programmer 22 may be accomplished by RF communication or proximal inductive interaction of external programmer 22 with IMD 16. This wireless communication is possible through the use of telemetry module 64. Accordingly, telemetry module 64 may be similar to the telemetry module contained within IMD 16. In alternative examples, programmer 22 may be capable of infrared communication or direct communication through a wired connection. In this manner, other external devices may be capable of communicating with programmer 22 without needing to establish a secure wireless connection.

Power source 68 delivers operating power to the components of programmer 22. Power source 68 may include a battery and a power generation circuit to produce the operating power. In some examples, the battery may be rechargeable to allow extended operation.

Figure 4:
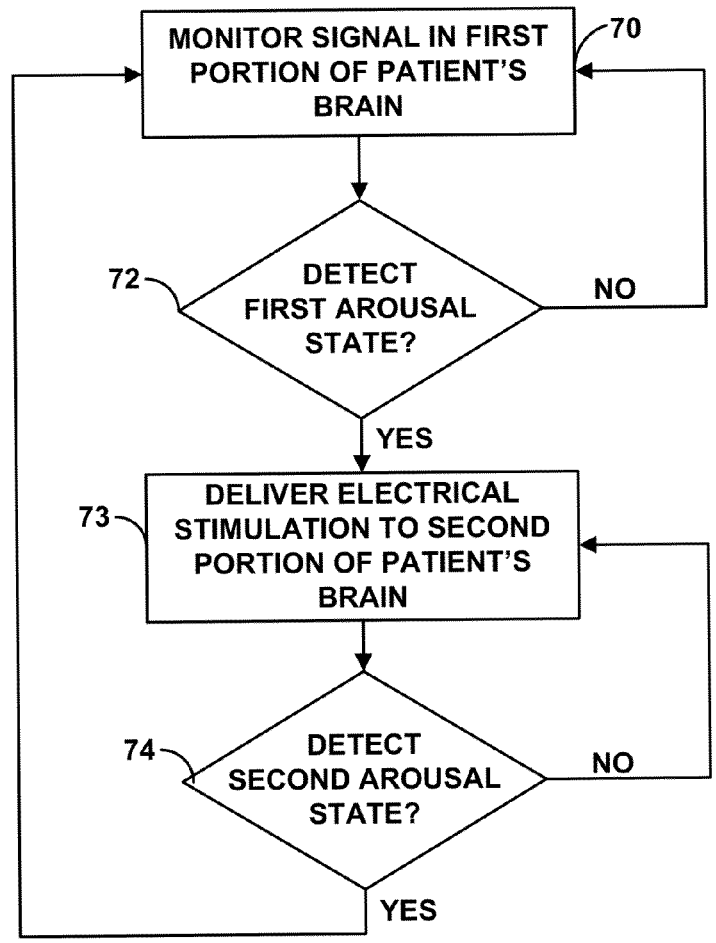
FIG. 4 is a flow diagram illustrating an example technique for inducing an arousal state in a brain of a patient to manage a cognitive disorder of the patient.

FIG. 4 is a flow diagram illustrating an example technique for inducing an change in an arousal state of brain 14 of patient 12, i.e., a change from a first arousal state to a second arousal state of brain 14. As discussed previously, a patient suffering from a cognitive disorder, e.g., Alzheimer's disease, may have reduced ability to enter an arousal state in which the patient is responsive to stimuli, e.g., vigilant, alert, and attentive to the surrounding environment and ongoing events. Consequently, inducing an increased arousal state in the brain of the patient may be useful for treating (e.g., mitigating the frequency or severity of symptoms) the cognitive disorder, which may result in increased cognitive functioning of the patient, e.g., increased memory processing and formation. While FIG. 4 is described with reference to processor 40 of IMD 16, in other examples, a processor of another device, such as processor 60 of external programmer 22, may perform any part of the technique shown in FIG. 4.

Processor 40 may determine that brain 14 is in a relatively low arousal state but that a relatively high arousal state may be more desirable for patient 12 to treat the patient's condition. In some examples, processor 40 may receive input from a user, e.g., from patient 12 or a clinician via user interface 66 of external programmer 22, indicating that patient 12 is in a situation or environment in which a relatively high arousal state may be more desirable than a relatively low arousal state. For example, a relatively high arousal state may be more desirable for patient 12 in situations or environments in which patient 12 would benefit from being responsive to stimuli, e.g., being attentive to and engaging in ongoing activities, in comparison to a situation or environment in which patient 12 need not be responsive to stimuli, e.g., when patient 12 is in a sleep state. As another example, processor 40 may sense a bioelectrical brain signal of patient 12 and determine an arousal state of brain 14 at any suitable frequency, such as about 1 Hz to about 100 Hz. Processor 40 may be programmed to control stimulation generator 42 to maintain the arousal state of patient 12 in a particular state (e.g., the second arousal state, which can be a relatively high arousal state).

In the example technique illustrated in FIG. 4, processor 40 monitors a bioelectrical brain signal indicative of electrical activity in a first portion of brain 14 of patient 12 (70). As discussed previously, the first portion of brain 14 may be a portion of brain 14 that includes an arousal neural network. In some examples, the first portion of brain 14 may include a relatively large portion of brain 14. In some examples, the first portion of brain 14 may include the thalamus and/or cortex.

Processor 40 may monitor the bioelectrical brain signal using any suitable technique. For example, in some examples, processor 40 monitors the bioelectrical brain signal using one or more of electrodes 24, 26 that are implanted proximate to (e.g., within) the first portion of brain 14. Sensing module 44 may sense the bioelectrical brain signal via the one or more electrodes 24, 26 and transmit the bioelectrical brain signal to processor 40 such that processor 40 can monitor the activity within the first portion of brain 14. In these examples, the bioelectrical brain signal may be any signal indicative of electrical activity sensed within brain 14, such as an ECoG signal, a LFP sensed from within one or more regions of brain 14, and/or action potentials from single cells within the brain 14.

In addition, as discussed previously, in some examples, therapy system 10 may include one or more external electrodes positioned outside of brain 14, e.g., on the outside of the cranium of patient 12, to sense bioelectrical brain signals generated by brain 14. The one or more external electrodes can detect activation of portions of brain 14 and, in some examples, may detect widespread activation of neural networks, e.g., arousal neural networks, within brain 14. In some examples, the external electrodes may transmit the sensed bioelectrical brain signals to processor 40 of IMD 16, and processor 40 can monitor the bioelectrical brain signals sensed by the external electrodes.

In the example technique illustrated in FIG. 4, processor 40 determines whether brain 14 is in a first arousal state based on at least one characteristic of the bioelectrical brain signal monitored by processor 40 (72). In some examples, processor 40 may analyze the bioelectrical brain signal to extract one or more particular values for characteristics, e.g., amplitude or frequency, of the bioelectrical brain signal, and may compare the values to one or more threshold values to determine whether brain 14 is in a particular arousal state, e.g., the first arousal state. For example, processor 40 may access one or more previously determined threshold values stored in arousal state information module 54 of memory 41 (FIG. 2) and compare the sensed values to the threshold values of the bioelectrical brain signal to determine whether the sensed values exceed or fall below a threshold value indicative of a particular arousal state of brain 14.

As an example, processor 40 may determine whether patient 12 is in the first arousal state based on determining whether the bioelectrical brain signal exhibits a relatively low frequency, e.g., less than about 7 Hertz, and a relatively large amplitude, e.g., greater than about 32 microvolts to about 120 microvolts, e.g., by comparing the sensed values to the threshold values stored by arousal state information module 54. In some examples, bioelectrical brain signals indicative of a relatively low arousal state may be characterized by a relatively low frequency and a relatively large amplitude (e.g., the absence of desynchronization or synchronization). Consequently, in response to determining that the bioelectrical brain signal exhibits a relatively low frequency and a relatively large amplitude (in comparison to the threshold values stored within arousal state information module 54), processor 40 may determine that brain 14 is in a relatively low arousal state. In other examples, processor 40 may implement other signal processing techniques, such as template matching, as described above with respect to FIG. 2.

As another example, processor 40 may determine whether patient 12 is in the first arousal state based on determining whether the bioelectrical brain signal sensed within the first portion of brain 14 exhibits a relatively high degree of phase locking of oscillations. In contrast, a relatively high arousal state may be characterized by reduced phase locking of brain signals in different regions of brain 14.

In examples in which the first arousal state is a relatively low arousal state, e.g., a state in which one or more symptoms of the patient's Alzheimer's disease can be observed, processor 40 may determine first portion of brain 14 is in the first arousal state by detecting disrupted frequency matching between electrical activity in the first portion of brain 14 and one or more other regions of brain 14. For example, two of electrodes 24, 26 may be implanted in two locations within brain 14, where one location is within the first portion of brain 14 and the other location is outside of the first portion of brain 14. Sensing module 44 may detect a first bioelectrical brain signal sensed with one of the electrodes 24, 26 implanted within the first portion of brain 14 and a second bioelectrical brain signal sensed with the other electrode 24, 26 implanted in another portion of brain 14. Sensing module 44 may subsequently transmit the first and second bioelectrical brain signals to processor 40.

In some examples, processor 40 analyzes the first and second bioelectrical brain signals to determine whether the first and second bioelectrical brain signals exhibit disrupted frequency matching. For example, processor 40 may compare frequency band characteristics of the first signal to frequency band characteristics of the second signal to determine whether the two signals (at the same point in time) are defined by substantially different frequencies, thereby disrupted frequency matching.

If processor 40 determines that brain 14 is not in the first arousal state based on the at least one characteristic of the bioelectrical brain signal, processor 40 continues to monitor the bioelectrical brain signal in the first portion of brain 14 (70). On the other hand, if processor 40 determines that brain 14 is in the first arousal state, processor 40 controls stimulation generator 42 to deliver electrical stimulation to a second portion of brain 14 to induce a second arousal state in brain 14 (73). Processor 40 can control stimulation generator 42 to deliver electrical stimulation to a second portion of brain 14 to induce a second arousal state in brain 14 (73) in response to the determination that brain 14 is in the first arousal state. For example, the determination that brain 14 is in the first arousal state be an input that causes processor 40 to control stimulation generator 42 to deliver electrical stimulation to a second portion of brain 14. In some examples, processor 40 can control stimulation generator 42 to deliver electrical stimulation to a second portion of brain 14 substantially immediately after detecting the first arousal state, such as within about 30 seconds of the detection of the first arousal state, such as about within 10 seconds or less, or about within 1 second.

As previously discussed, the second portion of brain 14 may be a portion of brain 14 that plays a role in activating an arousal neural network (e.g., an arousal neural network in the first portion of brain 14). In some examples, the second portion of brain 14 may include the anterior thalamic nucleus, the internal capsule, the cingulate cortex (including the anterior cingulate gyms), the formix, the mammillary bodies, the mammillothalamic tract (mammillothalamic fasciculus), the hippocampus, the Basal Nucleus of Meynert (NBM), the medial septal nucleus, the thalamic reticular nucleus the orbitofrontal cortex, the locus coeruleus, the raphe nucleus, the substantia nigra, the amygdala, the interior thalamus, the hypothalamus, and other portions of the thalamus and the limbic system.

In some examples, the second portion of the brain may be a more posterior region, in comparison to a more frontal region, such that electrical stimulation of the second portion activates a relatively large area within brain 14. That is, regions of brain 14 that are more posterior than frontal may be responsible for activation of larger portions of brain 14 (e.g., larger neural networks) and, consequently, stimulation of more posterior portions may cause activation of a larger portion of brain 14 than stimulation of more frontal portions. In some examples, the first portion of brain 14 may include the second portion of brain 14 while, in other examples, the first portion of brain 14 may exclude the second portion of brain 14.

As discussed above, while delivering stimulation directly to the first portion of the brain may be useful, it is believed that, in some cases, activating the arousal network of which the first portion of the brain is part by stimulating the second portion of the brain may be more effective in managing some neurological disorders, such as Alzheimer's disease, because the arousal of a larger region of brain 28 is activated by stimulating the second portion of brain 14. Increasing an arousal state of not only the first portion of brain 14 but other regions of brain 14 in conjunction with the first part may help improve the patient's cognition. In addition, delivering stimulation to the second portion of brain 14, which may activate a larger portion of the brain than delivering stimulation to the first portion, may be a more efficient use of stimulation energy.

Processor 40 may control stimulation generator 42 to deliver electrical stimulation defined by any stimulation parameters, e.g., frequency, amplitude, electrode combination, and the like, suitable for inducing the second arousal state in the first portion of brain 14. In some examples, processor 40 may access one or more stimulation programs stored in stimulation programs module 52 of memory 41 that are correlated to a particular arousal state and control stimulation generator 42 to deliver stimulation to brain 14 according to the stimulation programs.

Upon controlling delivery of electrical stimulation to the second portion of brain 14, processor 40 determines whether the second arousal state has been induced in brain 14 (74). Several example techniques for determining whether brain 14 is in the second arousal state are described below with respect to FIGS. 6A-6C. If processor 40 determines that brain 14 is not in the second arousal state, processor 40 may continue to control delivery of electrical stimulation to the second portion of brain 14 to induce the second arousal state (73). On the other hand, in the example technique illustrated in FIG. 4, if processor 40 determines that brain 14 is in the second arousal state, processor 40 may adjust the stimulation to the second portion of brain 14 in response to the determination (e.g., discontinue stimulation or reduce the intensity, such as by reducing the amplitude, frequency and/or other characteristics of the stimulation signal), and processor 40 may continue to monitor the bioelectrical brain signal in the first portion of brain 14 (70). In other examples, processor 40 may terminate the technique after detecting the second arousal state instead of continuing to monitor the bioelectrical brain signal in the first portion of brain 14.

Although the technique illustrated in FIG. 4 is described with reference to processor 40 of IMD 16, in other examples, the technique can be performed by another processor or component of therapy system 10, such as processor 60 of programmer 22.

FIG. 5 is a conceptual diagram of brain 14 illustrating several example neural connections within brain 14 that may play a role in inducing an increased arousal state. FIG. 5 illustrates a plurality of arousal networks, which includes a plurality of anatomical structures or regions of brain 14 that are connected by neural pathways. In the example illustrated in FIG. 5, the neural connections center around the thalamus and other structures located near the thalamus, e.g., the medial septal nucleus, the hypothalamus, the Basal Nucleus of Meynert, and the thalamic reticular nucleus, within brain 14.

As illustrated in FIG. 5, various structures within brain 14 may have neural pathways that extend outside of the boundaries of the particular structure in order to activate larger portions of brain 14. For example, as illustrated in FIG. 5, the hypothalamus may activate neural pathways that extend outward from the hypothalamus into the frontal cortex of brain 14. Similarly, as illustrated in FIG. 5, the Basal Nucleus of Meynert may activate neural pathways extending outward into the temporal cortex and the frontal cortex, the thalamus may activate neural pathways extending outward into the parietal cortex and the occipital cortex, etc. FIG. 5 also illustrates a relationship between the activation (e.g., by the delivery of stimulation) of the medial septal nucleus and the parietal cortex, occipital cortex, and temporal cortex. In addition, as illustrated in FIG. 5, the activation of the MRF may result in an increased arousal state in the thalamus and brainstem. The second portion of brain 14 to which stimulation is delivered in accordance with the technique shown in FIG. 5 can include or consist essentially of one or more of these structures that have neural pathways that extend outside of the boundaries of the particular structure in order to activate larger portions of brain 14.

In some examples, the neural pathways illustrated in FIG. 5 may be responsible for activation of one or more arousal neural networks within brain 14, which, as described herein, can be useful for treating a cognitive disorder of patient 12. That is, in some examples, some or all of the neural pathways illustrated in FIG. 5 may be arousal neural networks that are responsible for creating the arousal state of brain 14. As an example, in some patients, e.g., patient 12, the frontal cortex may be especially active in producing an increased arousal state in brain 14. Consequently, portions of brain 14 that project outward into the frontal cortex via neural networks, e.g., the Basal Nucleus of Meynert, the hypothalamus, etc., may be effective target tissue sites for stimulation that can induce an increased arousal state in brain 14.

In some examples, in order to monitor the efficacy of electrical stimulation delivered by IMD 16, processor 40 may determine whether the electrical stimulation delivered by stimulation generator 42 has effectively induced an increased arousal state in brain 14 to treat a cognitive disorder of patient 12. FIGS. 6A, 6B, and 6C are flow diagrams illustrating example techniques for determining whether brain 14 is in the increased arousal state (e.g., the second arousal state referred to in FIG. 4). The increased arousal state may be state in which the cognitive function of patient 14 is improved relative to the first arousal state. Although the techniques illustrated in FIGS. 6A, 6B, and 6C are described with reference to processor 40 of IMD 16, in other examples, the techniques can be performed by another processor or component of therapy system 10, such as processor 60 of programmer 22. In some examples, processor 40 of IMD 16 may implement any of the techniques shown in FIGS. 6A-6C to determine whether the stimulation delivered to a second portion of brain 14 induced a second arousal state in the first portion of brain 14.

As described above with respect to FIG. 4, in some examples, processor 40 may control stimulation generator 42 to generate and deliver stimulation to a second portion of brain 14 in response to determining a first portion of brain 14, which is different than the second portion, is in a first arousal state, e.g., a relatively low arousal state. The first and second arousal states may be associated with respective biomarkers, which may be stored by memory 41 of IMD 16 as arousal state information 54 (FIG. 2), by memory 62 of programmer 22 (FIG. 3), or a memory of another device.

FIG. 6A illustrates an example technique for determining that brain 14 is in the increased arousal state based on detecting desynchronization within the first portion of brain 14. As discussed above, in some examples, desynchronization of bioelectrical brain signals in a portion of brain 14 may be indicative of a relatively high arousal state of brain 14. Consequently, detecting desynchronization in a particular portion of brain 14 may be useful in determining that brain 14 is in an increased arousal state.

In the technique illustrated in FIG. 6A, processor 40 monitors a bioelectrical brain signal in the portion of brain 14 that includes an arousal neural network (76), e.g., referred to herein as the first portion of brain 14. For example, one or more of electrodes 24, 26 may be implanted within the portion of brain 14 that includes an arousal neural network, and sensing module 44 may detect the bioelectrical brain signal via the one or more electrodes 24, 26. Sensing module 44 may subsequently transmit the bioelectrical brain signal to processor 40 for analysis.

Desynchronization within the portion of brain 14 that includes an arousal neural network may generally refer to electrical activity within brain 14 characterized by relatively low amplitudes and relatively high frequencies. In some examples, the low amplitudes and high frequencies may be indicative of chaotic activity, which can indicate that brain 14 is relatively more responsive to stimuli.

Processor 40 can analyze the bioelectrical brain signal to determine whether the signal exhibits desynchronization characteristics. For example, processor 40 may analyze the bioelectrical brain signal to determine whether the signal exhibits a relatively low amplitude and a relatively high frequency (e.g., in the gamma and/or beta bands). The relatively high frequency can be indicated by increased neural activity in the local field potential range of about 16 Hz to about 200 Hz, although other frequencies are contemplated. In some examples, processor 40 may compare the amplitude and frequency values of the signal to previously determined amplitude, frequency threshold values that are indicative of desynchronization in order to determine whether the signal exhibits desynchronization characteristics. If the sensed signal exhibits relatively high frequency and relatively low amplitude characteristics, processor 40 may detect desynchronization (78). As discussed previously, desynchronization within portions of brain 14 may be indicative of an increased arousal state in brain 14, which may be useful in treating a cognitive disorder of patient 12. Thus, if processor 40 detects desynchronization based on characteristics of the sensed bioelectrical brain signal, processor 40 may determine that brain 14 is in an increased arousal state (also referred to herein as a "second" arousal state) (80).

In some examples, processor 40 can detect desynchronization based on input indicative of patient oriented behaviors, based on one or more physiological parameters and/or based on an evoked potential, as discussed above.

FIG. 6B illustrates an example technique for determining that brain 14 is in an increased arousal state based on detecting widespread activation of an arousal neural network within brain 14. As discussed previously, in some examples, multiple electrodes positioned outside of brain 14 (e.g., scalp electrodes) may be capable of detecting widespread activation of neural networks within brain 14. In some examples, activation of an arousal neural network and, consequently, an increased arousal state can be detected.

In the technique illustrated in FIG. 6B, processor 40 monitors bioelectrical brain signals detected by a set of external electrodes positioned outside of brain 14 (82). In some examples, therapy system 10 includes a plurality of external electrodes in addition to electrodes 24, 26 (implanted within brain 14). The external electrodes may be positioned at various points outside the cranium of patient 12 in order to externally sense bioelectrical signals (e.g., EEG signals) generated by brain 14. For example, the external electrodes may be positioned externally along the scalp of patient 12 at various points substantially surrounding brain 14 such that the external electrodes can detect bioelectrical signals generated within multiple portions of brain 14. In this way, the external electrodes may detect widespread activation of neural networks within brain 14, which may be useful in detecting activation of an arousal neural network within brain 14.

Therapy system 10 may monitor the bioelectrical brain signals sensed by the external electrodes in any suitable manner. For example, in some examples, the external electrodes may transmit the bioelectrical brain signals to processor 40 for analysis such that processor 40 can monitor the bioelectrical brain signals. In some examples, processor 40 may determine a relative value, e.g., an average value, a median value, etc., for a characteristic of the bioelectrical brain signals sensed by the plurality of external electrodes in order to monitor the activity within brain 14. That is, in some examples, processor 40 may analyze the bioelectrical brain signals sensed by each of the plurality of external electrodes and determine a relative value for a particular characteristic of the signal, e.g., frequency, amplitude, etc., based on each of the individual bioelectrical brain signals. In some examples, processor 40 can compare the relative value to one or more relative values for previously sensed bioelectrical brain signals to determine whether a change in the activity of brain 14 has occurred over time, e.g., whether an increased arousal state has been induced. In other examples, processor 40 may compare the relative value to one or more threshold relative values to determine whether the relative value exceeds a threshold that is indicative of a change in the activity of brain 14 over time or indicative of a particular arousal state of brain 14, such as a relatively high arousal state. As previously discussed, in some cases, an increased activity level in the gamma and/or beta bands (e.g., based on a comparison of the frequency of a bioelectrical brain signal to a threshold value), a decreased activity level in the delta and/or theta bands, or a combination thereof can be indicative of the second arousal state. In addition, in some cases, an increased activity level in the theta and/or delta bands, a decreased activity level in the gamma and/or beta bands, or a combination thereof can be indicative of the first arousal state.

Based on the bioelectrical brain signals sensed by the external electrodes, processor 40 may detect widespread activation of an arousal neural network within brain 14 (84). For example, processor 40 may monitor the bioelectrical brain signals sensed by the plurality of external electrodes and determine that the overall activity level within brain 14 or within a portion of brain 14 that includes an arousal neural network has increased, which may be indicative of an arousal state of brain 14. In some examples, processor 40 may determine that a relative value, e.g., an average value, of a characteristic of the bioelectrical brain signal has increased, e.g., by comparing the relative value to a stored threshold value, which can be indicative of widespread activation of an arousal neural network in brain 14.

Upon detecting activation of an arousal neural network via external electrodes, processor 40 determines that brain 14 is in an increased arousal state (86). Processor 40 or a user may then determine that therapy delivered via IMD 16 has been effective in inducing an increased arousal state to treat the cognitive disorder of patient 12.

FIG. 6C illustrates an example technique for determining that brain 14 is in an increased arousal state based on detecting a change in physiological parameter of patient 12 other than a bioelectrical brain signal. As discussed previously, in some examples, a physiological parameter of patient 12 can be indicative of an arousal state of patient 12, such that a change in the parameter may indicative of a change in an arousal state. In some examples, therapy system 10 includes a sensor 28 (FIG. 1) that generates a signal indicative of a physiological parameter of patient 12.

According to the technique illustrated in FIG. 6C, processor 40 monitors a physiological parameter of patient 12 using any suitable technique (88). In some examples, processor 40 monitors the physiological parameter based on a signal generated by sensor 28, and monitors the physiological parameter after delivering stimulation to the second portion of brain (block 74 in FIG. 4). In this way, processor 40 may monitor a physiological response of patient 12 to the electrical stimulation therapy based on a signal generated by sensor 28. In some examples, processor 40 monitors galvanic skin response, respiratory rate, heart rate, body temperature, and/or muscle activity of patient 12, which may change based on arousal state of patient 12. As an example, in some examples, patient 12 may exhibit increased galvanic skin response, respiratory rate, heart rate, body temperature, and/or muscle activity of patient 12 when the first portion of brain 14 is in an increased arousal state, and processor 40 can detect the change in physiological response in order to identify the increased arousal state. For ease of description, FIG. 6C will be described with respect to detecting a change in galvanic skin response of patient 12. However, in other examples, other physiological responses may be used in addition to or instead of galvanic skin response.

As discussed previously, the galvanic skin response of patient 12 is a measurement of the electrical conductance of the skin of patient 12, and may vary with the moisture level of the skin, e.g., as a result of perspiration. In some examples, an increased arousal state in the first portion of brain 14 may correlate to increased moisture level of the skin, e.g., increased sweating, of patient 12, resulting in increased galvanic skin response, e.g., electrical conductance of the skin, of patient 12. Consequently, an increased galvanic skin response of patient 12 may be indicative of increased state of arousal of brain 14.

In some examples, sensor 28 is positioned to measure galvanic skin response of patient 12. For example, an external sensor 28 may be placed in contact with the skin of patient 12 in order to measure the electrical conductance of the skin. External sensor 28 can transmit measurements of the skin conductance to processor 40 for analysis. For example, external sensor 28 can continuously sense and transmit measurements for the skin conductance to processor 40, and processor 40 can compare the measurements to previously sensed skin conductance measurements to determine whether a change in galvanic skin response has occurred over time, e.g., between two measurements collected at different points in time. In other examples, processor 40 may compare the measurements to previously determined threshold values that are indicative of arousal to determine whether brain 14 is in an increased arousal state. As an example, a galvanic skin response indicative of decreased skin resistance (decreased impedance) may be indicative of an increased arousal state. These values that are indicative of an increased arousal state may be stored by memory 41 of IMD 16, memory 62 of programmer 22 or a memory of another device.

Processor 40 may detect a change in physiological response of patient 12 based on monitoring the physiological response of patient 12 (90). For example, with respect to galvanic skin response, processor 40 may determine that a particular measurement value of skin conductance of patient 12 has changed in relation to a previously-measured value of skin conductance. That is, processor 40 may determine that the galvanic skin response of patient 12 has changed over time.

In some examples, based on detecting a particular change in the physiological response of patient 12, processor 40 may determine that brain 14 is in an increased arousal state (92). In some examples, in order to determine whether the arousal state of brain 14 has changed, processor 40 may determine whether the detected change in physiological response is sufficiently significant to indicate a change in arousal state of patient 12. That is, in some examples, a relatively small change in physiological response may not be sufficiently significant to indicate that the arousal state of patient 12 has changed, but a relatively large change in physiological response may be indicative of a change in arousal state.

In order to determine whether the change in physiological response is sufficiently significant to indicate a change in arousal state of patient 12, in some examples, processor 40 may determine the difference in measurement values detected at two points in time and compare the difference to a threshold value that has previously been determined to be indicative of a change in arousal state of patient 12. For example, in examples in which processor 40 monitors galvanic skin response, processor 40 may detect an increase in skin conductance between two skin conductance measurement values detected at two points in time. In order to determine whether the change is sufficient to indicate an increased state of arousal of brain 14, processor 40 may compare the change to a threshold value that has previously been determined to be indicative of an increase in arousal of brain 14. If processor 40 determines that the change in physiological response of patient 12 is sufficient to indicate an increased arousal state of brain 14, processor 40 determines that brain 14 is in an increased arousal state and, in some examples, that electrical stimulation delivered by IMD 16 has been effective in inducing the increased arousal state for treatment of the cognitive disorder of patient 12. In other examples, processor 40 does not determine whether there has been a change in the physiological parameter, but determines whether the physiological parameter is indicative of a particular arousal state of interest (e.g., a relatively high arousal state).

Other techniques can be used for detecting the increased arousal state (e.g., the second arousal state) of patient 12. In some examples, for example, patient 12 or a patient caretaker can provide input to programmer 22 that indicates certain patient states (e.g., feeling alert) that are indicative of the increased arousal state. As another example, programmer 22 may be configured to test the patient's reaction time (e.g., the time it takes patient 12 to push certain buttons or provide another input in response to flashing lights or other stimuli). Programmer 22 may transmit this input to IMD 16 via their respective telemetry modules 64, 48. Processor 40 or another processor (e.g., a processor of programmer 22) can determine whether patient 12 is in the increased arousal state based on the reaction time. The reaction times indicative of the increased arousal state can be stored by a memory of IMD 16 or a memory of another device such as programmer 22. Thus, upon determining that patient 12 reacted to the stimuli provided by programmer 22 within the predetermined time range associated with the increased arousal state in memory 41 or another memory, processor 40 may determine that patient 12 is in the relatively high arousal state (e.g., the second arousal state).

In other examples, processor 40 can detect an increased arousal state of patient 12 based on one or more physiological parameters of patient 12 that change as a function of the arousal state of patient 12. For example, sensing module 44 or another sensor separate from IMD 16 can generate a signal indicative of heart rate of patient 12 (e.g., an increased heart rate, such as a heart rate above a threshold or a certain change in heart rate over time, may be indicative of a relatively high arousal state). Other physiological parameters can include body temperature e.g., an increased temperature, such as a temperature above a threshold or a certain change in temperature over time, may be indicative of a relatively high arousal state), heart rate variability, and/or respiratory rate (e.g., an increased respiratory rate, such as a respiratory rate above a threshold or a certain change in respiratory rate over time, may be indicative of a relatively high arousal state). Physiological parameter values (e.g., specific values, range of values or certain changes in the values over time) indicative of the increased arousal state can be stored in memory 41 of IMD 16 or a memory of another device (e.g., programmer). Processor 40 can periodically or continuously monitor the one or more physiological parameters and, upon detecting the physiological parameter value(s) associated with the increased arousal state, processor 40 may determine that patient 12 is in the second arousal state.

Another technique for determining an arousal state of patient 12 can include determining the arousal state based on a stimulus induced evoked potential (also referred to as an evoked response). For example, processor 40 can control stimulation generator 42 (FIG. 2) to generate and deliver electrical stimulation to the first portion and/or second portion brain 14 of patient 12, and subsequently control sensing module 44 (FIG. 2) to sense the response of the first portion of brain 14 to the delivered stimulation. The response of the first portion of brain 14 to the delivered stimulation can be referred to as the evoked response. The amplitude of the evoked potential may be indicative of the arousal state. In this way, the evoked response of first portion of brain 14 may be used as a biomarker for a particular arousal state.

The electrical stimulation delivered to brain 14 to evoke the response can have any suitable stimulation parameter values, such as a relatively low frequency of about 2 Hz to about 10 Hz, although other frequency ranges may also be used. In some examples, the electrical stimulation delivered to brain 14 to evoke a response with which an arousal state of a first portion of brain 14 of patient 12 is determined can be configured to have therapeutic effects, while in other examples, the electrical stimulation delivered to brain 14 to evoke a response with which an arousal state of a first portion of brain 14 of patient 12 is determined may not have therapeutic effects.

In some examples, memory 41 may store evoked response amplitude values with a respective one of the first arousal state and the second arousal state. During therapy delivery, processor 40 can control stimulation generator 42 to generate and deliver electrical stimulation to the first portion and/or second portion brain 14 of patient 12, and subsequently control sensing module 44 to sense the response (e.g., the bioelectrical brain signal) of the first portion of brain 14 to the delivered stimulation, and, based on the amplitude of the response, processor 40 can determine the arousal state of patient 12. For example, processor 40 can compare the amplitude (e.g., the mean, median, highest or smallest amplitude of the brain signal within a certain time range of the delivered stimulation) of the response to the stored values to determine the arousal state of patient 12. In some examples, processor 40 may determine the arousal state of patient 12 in this manner to control delivery therapy to the second portion of brain 14 to modulate an arousal state of the first portion of brain 12.

The techniques described in this disclosure, including those attributed to programmer 22, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 22, any one or more parts of the techniques described herein may be implemented by a processor of one of IMD 16, programmer 22, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:
1. A method comprising:
 receiving, from a sensing module, a bioelectrical brain signal indicative of electrical activity in a first portion of a brain of a patient;
 determining, with a processor, that the brain of the patient is in a first arousal state based on the bioelectrical brain signal, wherein determining that the brain of the patient is in the first arousal state comprises detecting a biom- arker indicative of the first arousal state based on the bioelectrical brain signal; and controlling, with the processor, a stimulation module to deliver electrical stimulation to a second portion of the brain of the patient that is different than the first portion in response to determining that the first portion of the brain of the patient is in the first arousal state, wherein the electrical stimulation is configured to activate an arousal neural network in the first portion of the brain of the patient to induce a second arousal state in the brain of the patient, wherein the first portion of the brain of the patient exhibits a higher amount of electrical activity in the second arousal state than in the first arousal state, and wherein the electrical stimulation is configured to treat a cognitive disorder of the patient.

2. The method of claim 1, further comprising determining, with the processor, that the brain of the patient is in the second arousal state based on the bioelectrical brain signal.

3. The method of claim 2, wherein determining that the brain of the patient is in the second arousal state based on the bioelectrical brain signal comprises determining whether the bioelectrical brain signal exhibits a high frequency relative to a first threshold value and a low amplitude relative to a second threshold value, wherein the high frequency and the low amplitude are indicative of desynchronization within the first portion of the brain of the patient.

4. The method of claim 1, wherein the bioelectrical brain signal comprises at least one of an electroencephalogram (EEG) signal, an electrocorticogram (ECoG) signal, a local field potential (LFP) signal, or an action potential from a single cell within the patient's brain.

5. The method of claim 1, further comprising:
receiving a signal indicative of a physiological parameter of the patient; and
determining, with the processor, the brain of the patient is in the second arousal state based on the signal.

6. The method of claim 5, wherein the at least one physiological parameter comprises at least one of a galvanic skin response of the patient, a heart rate of the patient, a respiratory rate of the patient, a body temperature of the patient, or muscle activity of the patient.

7. The method of claim 1, wherein the bioelectrical brain signal comprises a first bioelectrical brain signal, the method further comprising:
receiving a second bioelectrical brain signal sensed via a plurality of external electrodes;
detecting, with the processor, widespread activation of the arousal neural network based on the second bioelectrical brain signal; and
determining, with the processor, that the brain of the patient is in the second arousal state based on detecting the widespread activation.

8. The method of claim 1, wherein detecting the biomarker indicative of the first arousal state based on the bioelectrical brain signal comprises determining that the bioelectrical brain signal exhibits a high amplitude relative to a first threshold value and a low frequency relative to a second threshold value, wherein the high amplitude and the low frequency are indicative of synchronization.

9. The method of claim 1, wherein the first portion of the brain of the patient comprises a thalamus.

10. The method of claim 1, wherein the first portion of the brain of the patient comprises a cortex.

11. The method of claim 1, wherein the second portion of the brain of the patient comprises at least one of the anterior thalamic nucleus, the internal capsule, the cingulate cortex, the formix, the mammillary bodies, the mammillothalamic tract, the hippocampus, the Basal Nucleus of Meynert, the medial septal nucleus, the thalamic reticular nucleus, the orbitofrontal cortex, the locus coeruleus, the raphe nucleus, the substantia nigra, the amygdala, the interior thalamus, the hypothalamus, and the thalamus.

12. The method of claim 1, further comprising, with the processor, adjusting the electrical stimulation delivered by the stimulation module based on determining that the brain of the patient is in the second arousal state.

13. The method of claim 1, wherein the first arousal state is characterized by slowing of the bioelectrical brain signal relative to the second arousal state.

14. The method of claim 1, wherein the cognitive disorder is Alzheimer's disease, and wherein detecting the biomarker indicative of the first arousal state based on the bioelectrical brain signal comprises detecting at least one of lack of normal, high frequency oscillations in the bioelectrical brain signal, disrupted frequency matching of oscillations in the bioelectrical brain signal between at least two regions of the brain of the patient, reduced phase locking of oscillations in the bioelectrical brain signal, or pathological synchronization in the bioelectrical brain signal between at least two regions of the brain of the patient.

15. The method of claim 1, wherein detecting a biomarker indicative of the first arousal state based on the bioelectrical brain signal comprises comparing the bioelectrical brain signal to a template and detecting a particular frequency domain characteristic indicative of the first arousal state based on the comparison.

16. The method of claim 1, wherein the first portion of the brain of the patient is a thalamus and the second portion of the brain of the patient is a medullary reticular formation.

17. The method of claim 1, wherein the first portion of the brain of the patient is a cortex and the second portion of the brain of the patient is at least one of a Basal Nucleus of Meynert or a hypothalamus.

18. A system comprising:
a sensing module configured to sense a bioelectrical brain signal indicative of electrical activity in a first portion of a brain of a patient;
a processor configured to determine that the brain of the patient is in a first arousal state based on the bioelectrical brain signal, wherein the processor is configured to determine that the brain of the patient is in the first arousal state by at least detecting a biomarker indicative of the first arousal state based on the bioelectrical brain signal; and
a stimulation generator configured to generate and deliver electrical stimulation to a second portion of the brain of the patient that is different than the first portion,
wherein the processor is configured to control the stimulation generator to deliver electrical stimulation to the second portion of the brain of the patient in response to determining that the first portion of the brain of the patient is in the first arousal state, wherein the electrical stimulation is configured to activate an arousal neural network in the first portion of the brain of the patient to induce a second arousal state in the brain of the patient, wherein the first portion of the brain of the patient exhibits a higher amount of electrical activity in the second arousal state than in the first arousal state, and wherein the electrical stimulation is configured to treat a cognitive disorder of the patient.

19. The system of claim 18, wherein the processor is configured to determine that the brain of the patient is in the second arousal state based on the bioelectrical brain signal.

20. The system of claim 19, wherein the processor is configured to determine that the brain of the patient is in the second arousal state by at least determining the bio electrical brain signal exhibits a high frequency relative to a first threshold value and a low amplitude relative to a second threshold value, wherein the high frequency and the low amplitude are indicative of desynchronization within the first portion of the brain of the patient.

21. The system of claim 18, further comprising an external sensor configured to generate a signal indicative of a physiological parameter of the patient, wherein the processor is configured to determine the brain of the patient is in the second arousal state based on the signal.

22. The system of claim 21, wherein the at least one physiological parameter comprises at least one of a galvanic skin response of the patient, a heart rate of the patient, a respiratory rate of the patient, a body temperature of the patient, or muscle activity of the patient.

23. The system of claim 18, wherein the bioelectrical brain signal comprises a first bioelectrical brain signal, wherein the system further comprises a plurality of external electrodes configured to sense a second bioelectrical brain signal, and wherein the processor is configured to detect widespread activation of the arousal neural network based on at least the second bioelectrical brain signal and determine that the brain of the patient is in the second arousal state based on detecting the widespread activation.

24. The system of claim 18, wherein the processor is configured to detect the biomarker indicative of the first arousal state based on the bioelectrical brain signal by at least determining that the bioelectrical brain signal exhibits a high amplitude relative to a first threshold value and a low frequency relative to a second threshold value, wherein the high amplitude and the low frequency are indicative of synchronization in the first portion of the brain of the patient.

25. The system of claim 18, wherein the first portion of the brain of the patient comprises at least one of one of a thalamus or a cortex.

26. The system of claim 18, wherein the second portion of the brain of the patient comprises at least one of the anterior thalamic nucleus, the internal capsule, the cingulate cortex, the formix, the mammillary bodies, the mammillothalamic tract, the hippocampus, the Basal Nucleus of Meynert, the medial septal nucleus, the thalamic reticular nucleus, the orbitofrontal cortex, the locus coeruleus, the raphe nucleus, the substantia nigra, the amygdala, the interior thalamus, the hypothalamus, and the thalamus.

27. The system of claim 18, wherein the processor is configured to adjust the electrical stimulation based on determining that the brain of the patient is in the second arousal state.

28. The system of claim 18, wherein the cognitive disorder is Alzheimer's disease, and wherein the processor is configured to detect the biomarker indicative of the first arousal state based on the bioelectrical brain signal by detecting at least one of lack of normal, high frequency oscillations in the bioelectrical brain signal, disrupted frequency matching of oscillations in the bioelectrical brain signal between at least two regions of the brain of the patient, reduced phase locking of oscillations in the bioelectrical brain signal, or pathological synchronization in the bioelectrical brain signal between at least two regions of the brain of the patient.

29. A non-transitory computer-readable medium comprising instructions that cause a programmable processor to:

receive, from a sensing module, a bioelectrical brain signal indicative of electrical activity in a first portion of a brain of a patient;
determine that the brain of the patient is in a first arousal state based on the bioelectrical brain signal by at least detecting a biomarker indicative of the first arousal state based on the bioelectrical brain signal; and
control a stimulation generator to deliver electrical stimulation to a second portion of the brain of the patient in response to determining that the first portion of the brain of the patient is in the first arousal state, wherein the electrical stimulation is configured to activate an arousal neural network in the first portion of the brain of the patient to induce a second arousal state in the brain of the patient, wherein the first portion of the brain of the patient exhibits a higher amount of electrical activity in the second arousal state than in the first arousal state, and wherein the electrical stimulation is configured to treat a cognitive disorder of the patient.

30. The non-transitory computer-readable medium of claim 29, further comprising instructions that cause the processor to determine that the brain of the patient is in the second arousal state based on the bioelectrical brain signal.

31. The non-transitory computer-readable medium of claim 29, further comprising instructions that cause the processor to:
receive a signal indicative of a physiological parameter of the patient; and
determine the brain of the patient is in the second arousal state based on the signal.

32. A system comprising:
means for receiving a bioelectrical brain signal indicative of electrical activity in a first portion of a brain of a patient;
means for determining that the brain of the patient is in a first arousal state based on the bioelectrical brain signal, wherein the means for determining that the brain of the patient is in a first arousal state based on the bioelectrical brain signal comprises means for detecting a biomarker indicative of the first arousal state based on the bioelectrical brain signal; and
means for controlling delivery of electrical stimulation to a second portion of the brain of the patient that is different than the first portion in response to determining that the first portion of the brain of the patient is in the first arousal state, wherein the electrical stimulation is configured to activate an arousal neural network in the first portion of the brain of the patient to induce a second arousal state in the brain of the patient, wherein the first portion of the brain of the patient exhibits a higher amount of electrical activity in the second arousal state than in the first arousal state, and wherein the electrical stimulation is configured to treat a cognitive disorder of the patient.

33. The system of claim 32, further comprising means for determining that the brain of the patient is in the second arousal state based on the bioelectrical brain signal.

34. The system of claim 32, further comprising:
means for receiving a signal indicative of a physiological parameter of the patient; and
means for determining that the brain of the patient is in the second arousal state based on the signal indicative of the physiological parameter of the patient.

* * * * *